US009993642B2

(12) United States Patent
Gerasimenko et al.

(10) Patent No.: US 9,993,642 B2
(45) Date of Patent: *Jun. 12, 2018

(54) MULTI-SITE TRANSCUTANEOUS ELECTRICAL STIMULATION OF THE SPINAL CORD FOR FACILITATION OF LOCOMOTION

(71) Applicant: The Regents of the University of California, Oakland, CA (US)

(72) Inventors: Yury Gerasimenko, Los Angeles, CA (US); Victor Reggie Edgerton, Los Angeles, CA (US); Roland R. Roy, Playa Vista, CA (US); Daniel C. Lu, Rancho Palos Verdes, CA (US)

(73) Assignee: The Regents of the University of California, Oakland, CA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/775,618

(22) PCT Filed: Mar. 14, 2014

(86) PCT No.: PCT/US2014/029340
§ 371 (c)(1),
(2) Date: Sep. 11, 2015

(87) PCT Pub. No.: WO2014/144785
PCT Pub. Date: Sep. 18, 2014

(65) Prior Publication Data
US 2016/0030737 A1 Feb. 4, 2016

Related U.S. Application Data

(60) Provisional application No. 61/802,034, filed on Mar. 15, 2013.

(51) Int. Cl.
*A61N 1/36* (2006.01)
*A61N 1/04* (2006.01)
(Continued)

(52) U.S. Cl.
CPC .......... *A61N 1/36003* (2013.01); *A61K 31/00* (2013.01); *A61K 31/197* (2013.01);
(Continued)

(58) Field of Classification Search
CPC .......... A61N 1/04; A61N 1/0456; A61N 1/36; A61N 1/36003; A61N 1/36014
(Continued)

(56) References Cited

U.S. PATENT DOCUMENTS 3,543,761 A 12/1970 Bradley
3,662,758 A 5/1972 Glover
(Continued)

FOREIGN PATENT DOCUMENTS

AU 2012204526 A1 7/2013
CA 2 823 592 A1 7/2012
(Continued)

OTHER PUBLICATIONS

U.S. Office Action dated Apr. 8, 2015 issued in U.S. Appl. No. 14/355,812.
(Continued)

*Primary Examiner* — Christopher A Flory
(74) *Attorney, Agent, or Firm* — Tom Hunter; Weaver Austin Villeneuve & Sampson LLP

(57) ABSTRACT

In various embodiments, non-invasive methods to induce motor control in a mammal subject to spinal cord or other neurological injuries are provided. In some embodiments the methods involve administering transcutaneous electrical spi-
(Continued)

nal cord stimulation (tSCS) to the mammal at a frequency and intensity that induces locomotor activity.

23 Claims, 8 Drawing Sheets

(51) Int. Cl.
- *A61K 31/00* (2006.01)
- *A61K 31/197* (2006.01)
- *G06F 19/00* (2018.01)

(52) U.S. Cl.
CPC ....... *A61N 1/0456* (2013.01); *A61N 1/36014* (2013.01); *G06F 19/34* (2013.01); *A63B 2213/004* (2013.01)

(58) Field of Classification Search
USPC .......................................................... 607/48
See application file for complete search history.

(56) References Cited

U.S. PATENT DOCUMENTS

| | | | |
|---|---|---|---|
| 3,724,467 A | 4/1973 | Avery et al. | |
| 4,044,774 A | 8/1977 | Corbin et al. | |
| 4,102,344 A | 7/1978 | Conway et al. | |
| 4,141,365 A | 2/1979 | Fischell et al. | |
| 4,285,347 A | 8/1981 | Hess | |
| 4,340,063 A | 7/1982 | Maurer | |
| 4,379,462 A | 4/1983 | Borkan et al. | |
| 4,414,986 A | 11/1983 | Dickhudt et al. | |
| 4,538,624 A | 9/1985 | Tarjan | |
| 4,549,556 A | 10/1985 | Tajan et al. | |
| 4,559,948 A * | 12/1985 | Liss | A61N 1/36021 607/46 |
| 4,800,898 A | 1/1989 | Hess et al. | |
| 4,934,368 A | 6/1990 | Lynch | |
| 4,969,452 A | 11/1990 | Petrofsky et al. | |
| 5,002,053 A * | 3/1991 | Garcia-Rill | A61N 1/36003 607/49 |
| 5,031,618 A | 7/1991 | Mullett | |
| 5,081,989 A | 1/1992 | Graupe et al. | |
| 5,121,754 A | 6/1992 | Mullett | |
| 5,344,439 A | 9/1994 | Otten | |
| 5,354,320 A | 10/1994 | Schaldach et al. | |
| 5,374,285 A | 12/1994 | Vaiani et al. | |
| 5,417,719 A | 5/1995 | Hull et al. | |
| 5,476,441 A | 12/1995 | Durfee et al. | |
| 5,562,718 A | 10/1996 | Palermo | |
| 5,643,330 A | 7/1997 | Holsheimer et al. | |
| 5,733,322 A | 3/1998 | Starkebaum | |
| 5,983,141 A | 11/1999 | Sluijter et al. | |
| 6,066,163 A | 5/2000 | John | |
| 6,104,957 A | 8/2000 | Alo et al. | |
| 6,122,548 A | 9/2000 | Starkebaum et al. | |
| 6,308,103 B1 | 10/2001 | Gielen | |
| 6,319,241 B1 | 11/2001 | King et al. | |
| 6,470,213 B1 | 10/2002 | Alley | |
| 6,503,231 B1 | 1/2003 | Prausnitz et al. | |
| 6,551,849 B1 | 4/2003 | Kenney | |
| 6,587,724 B2 | 7/2003 | Mann | |
| 6,662,053 B2 | 12/2003 | Borkan | |
| 6,666,831 B1 | 12/2003 | Edgerton et al. | |
| 6,685,729 B2 | 2/2004 | Gonzalez | |
| 6,819,956 B2 | 11/2004 | DiLorenzo | |
| 6,839,594 B2 | 1/2005 | Cohen et al. | |
| 6,871,099 B1 | 3/2005 | Whitehurst et al. | |
| 6,892,098 B2 * | 5/2005 | Ayal | A61N 1/36003 607/45 |
| 6,895,280 B2 | 5/2005 | Meadows et al. | |
| 6,895,283 B2 | 5/2005 | Erickson et al. | |
| 6,937,891 B2 | 8/2005 | Leinders et al. | |
| 6,950,706 B2 | 9/2005 | Rodriguez et al. | |
| 6,975,907 B2 | 12/2005 | Zanakis et al. | |
| 6,988,006 B2 | 1/2006 | King et al. | |
| 6,999,820 B2 | 2/2006 | Jordan | |
| 7,020,521 B1 | 3/2006 | Brewer et al. | |
| 7,024,247 B2 | 4/2006 | Gliner et al. | |
| 7,035,690 B2 | 4/2006 | Goetz | |
| 7,047,084 B2 | 5/2006 | Erickson et al. | |
| 7,065,408 B2 * | 6/2006 | Herman | A61N 1/3604 482/54 |
| 7,096,070 B1 | 8/2006 | Jenkins et al. | |
| 7,110,820 B2 | 9/2006 | Tcheng et al. | |
| 7,127,287 B2 | 10/2006 | Duncan et al. | |
| 7,127,296 B2 | 10/2006 | Bradley | |
| 7,127,297 B2 | 10/2006 | Law et al. | |
| 7,153,242 B2 | 12/2006 | Goffer | |
| 7,184,837 B2 | 2/2007 | Goetz | |
| 7,200,443 B2 * | 4/2007 | Faul | A61N 1/36007 607/40 |
| 7,209,787 B2 | 4/2007 | DiLorenzo | |
| 7,228,179 B2 | 6/2007 | Campen et al. | |
| 7,239,920 B1 | 7/2007 | Thacker et al. | |
| 7,251,529 B2 | 7/2007 | Greenwood-Van Meerveld | |
| 7,252,090 B2 | 8/2007 | Goetz | |
| 7,313,440 B2 | 12/2007 | Miesel et al. | |
| 7,324,853 B2 * | 1/2008 | Ayal | A61N 1/36003 607/45 |
| 7,330,760 B2 | 2/2008 | Heruth et al. | |
| 7,337,005 B2 | 2/2008 | Kim et al. | |
| 7,337,006 B2 | 2/2008 | Kim et al. | |
| 7,381,192 B2 * | 6/2008 | Brodard | A61H 1/0255 601/33 |
| 7,415,309 B2 | 8/2008 | Mcintyre | |
| 7,463,928 B2 | 12/2008 | Lee et al. | |
| 7,467,016 B2 | 12/2008 | Colborn | |
| 7,493,170 B1 | 2/2009 | Segel et al. | |
| 7,496,404 B2 * | 2/2009 | Meadows | A61N 1/0553 607/43 |
| 7,502,652 B2 | 3/2009 | Gaunt et al. | |
| 7,536,226 B2 | 5/2009 | Williams et al. | |
| 7,544,185 B2 | 6/2009 | Bengtsson | |
| 7,584,000 B2 | 9/2009 | Erickson | |
| 7,590,454 B2 | 9/2009 | Garabedian et al. | |
| 7,603,178 B2 | 10/2009 | North et al. | |
| 7,628,750 B2 | 12/2009 | Cohen et al. | |
| 7,660,636 B2 | 2/2010 | Castel et al. | |
| 7,697,995 B2 | 4/2010 | Cross et al. | |
| 7,729,781 B2 | 6/2010 | Swoyer et al. | |
| 7,734,340 B2 | 6/2010 | De Ridder | |
| 7,734,351 B2 | 6/2010 | Testerman et al. | |
| 7,769,463 B2 | 8/2010 | Katsnelson | |
| 7,797,057 B2 | 9/2010 | Harris | |
| 7,801,601 B2 | 9/2010 | Maschino et al. | |
| 7,813,803 B2 | 10/2010 | Heruth et al. | |
| 7,856,264 B2 | 12/2010 | Firlik et al. | |
| 7,877,146 B2 * | 1/2011 | Rezai | A61B 5/411 607/42 |
| 7,890,182 B2 | 2/2011 | Parramon et al. | |
| 7,949,395 B2 | 5/2011 | Kuzma | |
| 7,949,403 B2 | 5/2011 | Palermo et al. | |
| 7,987,000 B2 | 7/2011 | Moffitt et al. | |
| 7,991,465 B2 | 8/2011 | Bartic et al. | |
| 8,019,427 B2 | 9/2011 | Moffitt | |
| 8,050,773 B2 | 11/2011 | Zhu | |
| 8,108,052 B2 | 1/2012 | Boling | |
| 8,131,358 B2 | 3/2012 | Moffitt et al. | |
| 8,155,750 B2 | 4/2012 | Jaax et al. | |
| 8,170,660 B2 | 5/2012 | Dacey, Jr. et al. | |
| 8,190,262 B2 | 5/2012 | Gerber et al. | |
| 8,195,304 B2 | 6/2012 | Strother et al. | |
| 8,229,565 B2 * | 7/2012 | Kim | A61N 1/0558 607/46 |
| 8,239,038 B2 | 8/2012 | Wolf, II | |
| 8,260,436 B2 | 9/2012 | Gerber et al. | |
| 8,271,099 B1 | 9/2012 | Swanson | |
| 8,295,936 B2 | 10/2012 | Wahlstrand et al. | |
| 8,311,644 B2 | 11/2012 | Moffitt et al. | |
| 8,332,029 B2 | 12/2012 | Glukhovsky et al. | |
| 8,346,366 B2 | 1/2013 | Arle et al. | |
| 8,352,036 B2 | 1/2013 | DiMarco et al. | |
| 8,355,791 B2 | 1/2013 | Moffitt | |

(56) References Cited

U.S. PATENT DOCUMENTS

| | | | |
|---|---|---|---|
| 8,355,797 B2 | 1/2013 | Caparso et al. | |
| 8,364,273 B2 | 1/2013 | De Ridder | |
| 8,369,961 B2 | 2/2013 | Christman et al. | |
| 8,412,345 B2 | 4/2013 | Moffitt | |
| 8,428,728 B2 * | 4/2013 | Sachs | A61N 1/36067 607/43 |
| 8,442,655 B2 | 5/2013 | Moffitt et al. | |
| 8,452,406 B2 | 5/2013 | Arcot-Krishmamurthy et al. | |
| 8,588,884 B2 | 11/2013 | Hegde et al. | |
| 8,700,145 B2 | 4/2014 | Kilgard et al. | |
| 8,712,546 B2 * | 4/2014 | Kim | A61N 1/0558 607/118 |
| 8,750,957 B2 | 6/2014 | Tang et al. | |
| 8,805,542 B2 * | 8/2014 | Tai | A61N 1/0553 607/116 |
| 9,101,769 B2 | 8/2015 | Edgerton et al. | |
| 9,205,259 B2 * | 12/2015 | Kim | A61N 1/0558 |
| 9,205,260 B2 * | 12/2015 | Kim | A61N 1/0558 |
| 9,205,261 B2 * | 12/2015 | Kim | A61N 1/36071 |
| 9,272,143 B2 * | 3/2016 | Libbus | A61N 1/36114 |
| 9,393,409 B2 | 7/2016 | Edgerton et al. | |
| 9,415,218 B2 | 8/2016 | Edgerton et al. | |
| 2002/0055779 A1 * | 5/2002 | Andrews | A61N 1/36014 623/11.11 |
| 2002/0111661 A1 | 8/2002 | Cross et al. | |
| 2002/0115945 A1 * | 8/2002 | Herman | A61H 3/00 601/15 |
| 2002/0193843 A1 | 12/2002 | Hill et al. | |
| 2003/0032992 A1 | 2/2003 | Thacker et al. | |
| 2003/0078633 A1 | 4/2003 | Firlik et al. | |
| 2003/0100933 A1 * | 5/2003 | Ayal | A61N 1/36003 607/48 |
| 2003/0220679 A1 | 11/2003 | Han | |
| 2003/0233137 A1 | 12/2003 | Paul, Jr. | |
| 2004/0039425 A1 | 2/2004 | Greenwood-Van Meerveld | |
| 2004/0044380 A1 | 3/2004 | Bruninga et al. | |
| 2004/0111118 A1 | 6/2004 | Hill et al. | |
| 2004/0122483 A1 | 6/2004 | Nathan et al. | |
| 2004/0127954 A1 * | 7/2004 | McDonald, III | A61H 39/002 607/48 |
| 2004/0133248 A1 | 7/2004 | Frei et al. | |
| 2004/0138518 A1 | 7/2004 | Rise et al. | |
| 2005/0004622 A1 | 1/2005 | Cullen et al. | |
| 2005/0075669 A1 | 4/2005 | King | |
| 2005/0075678 A1 | 4/2005 | Faul | |
| 2005/0102007 A1 * | 5/2005 | Ayal | A61N 1/36003 607/48 |
| 2005/0113882 A1 | 5/2005 | Cameron et al. | |
| 2005/0119713 A1 | 6/2005 | Whitehurst et al. | |
| 2005/0125045 A1 | 6/2005 | Brighton et al. | |
| 2005/0209655 A1 | 9/2005 | Bradley et al. | |
| 2005/0246004 A1 | 11/2005 | Cameron et al. | |
| 2006/0003090 A1 | 1/2006 | Rodger et al. | |
| 2006/0041295 A1 | 2/2006 | Osypka | |
| 2006/0089696 A1 | 4/2006 | Olsen et al. | |
| 2006/0100671 A1 | 5/2006 | Ridder | |
| 2006/0111754 A1 * | 5/2006 | Rezai | A61B 5/411 607/41 |
| 2006/0122678 A1 | 6/2006 | Olsen et al. | |
| 2006/0142816 A1 | 6/2006 | Fruitman | |
| 2006/0142822 A1 * | 6/2006 | Tulgar | A61N 1/08 607/61 |
| 2006/0149337 A1 | 7/2006 | John | |
| 2006/0239482 A1 | 10/2006 | Hatoum | |
| 2007/0016097 A1 | 1/2007 | Farquhar et al. | |
| 2007/0016266 A1 | 1/2007 | Paul, Jr. | |
| 2007/0049814 A1 * | 3/2007 | Muccio | A61N 1/0452 600/388 |
| 2007/0055337 A1 | 3/2007 | Tanrisever | |
| 2007/0060954 A1 * | 3/2007 | Cameron | A61N 1/0553 607/2 |
| 2007/0060980 A1 | 3/2007 | Strother et al. | |
| 2007/0073357 A1 | 3/2007 | Rooney et al. | |
| 2007/0083240 A1 | 4/2007 | Peterson et al. | |
| 2007/0156179 A1 | 7/2007 | Karashurov | |
| 2007/0179534 A1 | 8/2007 | Firlik et al. | |
| 2007/0191709 A1 | 8/2007 | Swanson | |
| 2007/0208381 A1 | 9/2007 | Hill et al. | |
| 2007/0233204 A1 | 10/2007 | Lima et al. | |
| 2007/0255372 A1 | 11/2007 | Metzler et al. | |
| 2007/0265679 A1 | 11/2007 | Bradley et al. | |
| 2007/0265691 A1 | 11/2007 | Swanson | |
| 2007/0276449 A1 | 11/2007 | Gunter et al. | |
| 2007/0276450 A1 | 11/2007 | Meadows et al. | |
| 2008/0021513 A1 | 1/2008 | Thacker et al. | |
| 2008/0046049 A1 | 2/2008 | Skubitz et al. | |
| 2008/0051851 A1 * | 2/2008 | Lin | A61N 1/05 607/42 |
| 2008/0071325 A1 | 3/2008 | Bradley | |
| 2008/0103579 A1 | 5/2008 | Gerber | |
| 2008/0140152 A1 | 6/2008 | Imran et al. | |
| 2008/0140169 A1 | 6/2008 | Imran | |
| 2008/0147143 A1 | 6/2008 | Popovic et al. | |
| 2008/0154329 A1 | 6/2008 | Pyles et al. | |
| 2008/0183224 A1 | 7/2008 | Barolat | |
| 2008/0207985 A1 | 8/2008 | Farone | |
| 2008/0215113 A1 | 9/2008 | Pawlowicz | |
| 2008/0221653 A1 | 9/2008 | Agrawal et al. | |
| 2008/0228250 A1 | 9/2008 | Mironer | |
| 2008/0234791 A1 | 9/2008 | Arle et al. | |
| 2008/0279896 A1 | 11/2008 | Heinen et al. | |
| 2009/0012436 A1 | 1/2009 | Lanfermann et al. | |
| 2009/0093854 A1 | 4/2009 | Leung et al. | |
| 2009/0112281 A1 | 4/2009 | Miyazawa et al. | |
| 2009/0118365 A1 * | 5/2009 | Benson, III | A61K 31/27 514/487 |
| 2009/0198305 A1 | 8/2009 | Naroditsky et al. | |
| 2009/0204173 A1 | 8/2009 | Fang et al. | |
| 2009/0270960 A1 | 10/2009 | Zhao et al. | |
| 2009/0281599 A1 | 11/2009 | Thacker et al. | |
| 2009/0299166 A1 | 12/2009 | Nishida et al. | |
| 2009/0299167 A1 | 12/2009 | Seymour | |
| 2009/0306491 A1 | 12/2009 | Haggers | |
| 2010/0004715 A1 | 1/2010 | Fahey | |
| 2010/0023103 A1 | 1/2010 | Elborno | |
| 2010/0042193 A1 | 2/2010 | Slavin | |
| 2010/0070007 A1 | 3/2010 | Parker et al. | |
| 2010/0114239 A1 * | 5/2010 | McDonald, III | A61H 39/002 607/48 |
| 2010/0125313 A1 | 5/2010 | Lee et al. | |
| 2010/0137938 A1 | 6/2010 | Kishawi et al. | |
| 2010/0145428 A1 * | 6/2010 | Cameron | A61N 1/0553 607/117 |
| 2010/0152811 A1 | 6/2010 | Flaherty | |
| 2010/0185253 A1 * | 7/2010 | Dimarco | A61N 1/0553 607/42 |
| 2010/0198298 A1 * | 8/2010 | Glukhovsky | A61N 1/36021 607/46 |
| 2010/0217355 A1 | 8/2010 | Tass et al. | |
| 2010/0241191 A1 | 9/2010 | Testerman et al. | |
| 2010/0268299 A1 | 10/2010 | Farone | |
| 2010/0274312 A1 | 10/2010 | Alataris et al. | |
| 2010/0305660 A1 | 12/2010 | Hegi | |
| 2010/0318168 A1 | 12/2010 | Bighetti | |
| 2010/0331925 A1 | 12/2010 | Peterson | |
| 2011/0029040 A1 | 2/2011 | Walker et al. | |
| 2011/0040349 A1 * | 2/2011 | Graupe | A61N 1/36003 607/49 |
| 2011/0054567 A1 | 3/2011 | Lane et al. | |
| 2011/0054568 A1 | 3/2011 | Lane et al. | |
| 2011/0054579 A1 | 3/2011 | Kumar et al. | |
| 2011/0125203 A1 * | 5/2011 | Simon | A61N 1/40 607/2 |
| 2011/0130804 A1 | 6/2011 | Lin et al. | |
| 2011/0152967 A1 * | 6/2011 | Simon | A61N 1/40 607/45 |
| 2011/0160810 A1 | 6/2011 | Griffith | |
| 2011/0166546 A1 * | 7/2011 | Jaax | A61N 1/36082 604/500 |
| 2011/0184488 A1 | 7/2011 | De Ridder | |
| 2011/0184489 A1 * | 7/2011 | Nicolelis | A61N 1/36025 607/48 |

(56) References Cited

U.S. PATENT DOCUMENTS

| | | | |
|---|---|---|---|
| 2011/0218594 A1 | 9/2011 | Doran et al. | |
| 2011/0224665 A1 | 9/2011 | Crosby et al. | |
| 2011/0224753 A1* | 9/2011 | Palermo | A61N 1/0452 607/45 |
| 2011/0224757 A1 | 9/2011 | Zdeblick et al. | |
| 2011/0230701 A1* | 9/2011 | Simon | A61N 1/36021 600/9 |
| 2011/0245734 A1* | 10/2011 | Wagner | A61N 1/36025 601/2 |
| 2011/0276107 A1* | 11/2011 | Simon | A61N 1/36021 607/46 |
| 2012/0006793 A1 | 1/2012 | Swanson | |
| 2012/0029528 A1 | 2/2012 | Macdonald et al. | |
| 2012/0035684 A1 | 2/2012 | Thompson et al. | |
| 2012/0101326 A1* | 4/2012 | Simon | A61N 1/36007 600/9 |
| 2012/0109251 A1 | 5/2012 | Lebedev et al. | |
| 2012/0109295 A1 | 5/2012 | Fan | |
| 2012/0123293 A1* | 5/2012 | Shah | A61N 1/0551 600/554 |
| 2012/0165899 A1 | 6/2012 | Gliner | |
| 2012/0172946 A1 | 7/2012 | Altaris et al. | |
| 2012/0179222 A1 | 7/2012 | Jaax et al. | |
| 2012/0185020 A1 | 7/2012 | Simon et al. | |
| 2012/0232615 A1 | 9/2012 | Barolat et al. | |
| 2012/0252874 A1* | 10/2012 | Feinstein | C12N 15/111 514/44 A |
| 2012/0259380 A1 | 10/2012 | Pyles | |
| 2012/0277824 A1* | 11/2012 | Li | A61N 1/36003 607/48 |
| 2012/0283697 A1* | 11/2012 | Kim | A61N 1/0558 604/506 |
| 2012/0283797 A1 | 11/2012 | De Ridder | |
| 2012/0310305 A1 | 12/2012 | Kaula et al. | |
| 2012/0330391 A1 | 12/2012 | Bradley et al. | |
| 2013/0013041 A1* | 1/2013 | Glukhovsky | A61N 1/36021 607/116 |
| 2013/0030319 A1 | 1/2013 | Hettrick et al. | |
| 2013/0030501 A1 | 1/2013 | Feler et al. | |
| 2013/0066392 A1* | 3/2013 | Simon | A61N 1/40 607/45 |
| 2013/0085317 A1* | 4/2013 | Feinstein | A61F 5/01 600/14 |
| 2013/0110196 A1 | 5/2013 | Alataris et al. | |
| 2013/0123568 A1* | 5/2013 | Hamilton | A61N 1/36003 600/13 |
| 2013/0165991 A1* | 6/2013 | Kim | A61N 1/36071 607/46 |
| 2013/0197408 A1 | 8/2013 | Goldfarb et al. | |
| 2013/0253299 A1* | 9/2013 | Weber | A61B 5/4519 600/377 |
| 2013/0253611 A1 | 9/2013 | Lee et al. | |
| 2013/0268016 A1 | 10/2013 | Xi et al. | |
| 2013/0268021 A1 | 10/2013 | Moffitt | |
| 2013/0281890 A1* | 10/2013 | Mishelevich | A61N 2/002 601/2 |
| 2013/0303873 A1* | 11/2013 | Voros | A61B 5/04001 600/377 |
| 2013/0304159 A1* | 11/2013 | Simon | A61N 1/40 607/65 |
| 2013/0310911 A1* | 11/2013 | Tai | A61N 1/0553 607/117 |
| 2014/0031893 A1 | 1/2014 | Walker et al. | |
| 2014/0046407 A1* | 2/2014 | Ben-Ezra | A61N 1/0556 607/62 |
| 2014/0058490 A1 | 2/2014 | DiMarco | |
| 2014/0066950 A1 | 3/2014 | Macdonald et al. | |
| 2014/0067007 A1 | 3/2014 | Drees et al. | |
| 2014/0067354 A1 | 3/2014 | Kaula et al. | |
| 2014/0081071 A1* | 3/2014 | Simon | A61N 1/36021 600/13 |
| 2014/0100633 A1* | 4/2014 | Mann | A61N 1/0551 607/59 |
| 2014/0107397 A1* | 4/2014 | Simon | A61N 1/36021 600/9 |
| 2014/0107398 A1* | 4/2014 | Simon | A61N 1/36021 600/13 |
| 2014/0114374 A1 | 4/2014 | Rooney et al. | |
| 2014/0163640 A1* | 6/2014 | Edgerton | A61N 1/0551 607/48 |
| 2014/0180361 A1 | 6/2014 | Burdick et al. | |
| 2014/0213842 A1* | 7/2014 | Simon | A61N 1/36021 600/13 |
| 2014/0236257 A1* | 8/2014 | Parker | A61B 5/04001 607/46 |
| 2014/0296752 A1 | 10/2014 | Edgerton et al. | |
| 2014/0303901 A1* | 10/2014 | Sadeh | G06F 19/22 702/19 |
| 2014/0316484 A1* | 10/2014 | Edgerton | A61N 1/36025 607/46 |
| 2014/0316503 A1 | 10/2014 | Tai et al. | |
| 2014/0324118 A1* | 10/2014 | Simon | A61N 1/36021 607/46 |
| 2014/0330335 A1* | 11/2014 | Errico | A61N 1/36025 607/45 |
| 2014/0357936 A1* | 12/2014 | Simon | A61N 1/40 600/13 |
| 2015/0065559 A1* | 3/2015 | Feinstein | C12N 15/111 514/44 A |
| 2015/0165226 A1* | 6/2015 | Simon | A61N 1/40 600/13 |
| 2015/0182784 A1* | 7/2015 | Barriskill | A61N 1/36003 607/3 |
| 2015/0231396 A1* | 8/2015 | Burdick | A61N 1/0553 607/48 |
| 2015/0265830 A1* | 9/2015 | Simon | A61N 1/0456 600/13 |
| 2016/0030737 A1* | 2/2016 | Gerasimenko | A61N 1/36003 607/48 |
| 2016/0030748 A1* | 2/2016 | Edgerton | A61N 1/0551 607/48 |
| 2016/0045727 A1* | 2/2016 | Rezai | A61N 1/36139 607/62 |
| 2016/0045731 A1* | 2/2016 | Simon | A61N 1/36007 600/9 |
| 2016/0121109 A1* | 5/2016 | Edgerton | A61N 1/36003 607/45 |
| 2016/0121116 A1* | 5/2016 | Simon | A61N 1/36021 607/46 |
| 2016/0175586 A1* | 6/2016 | Edgerton | A61N 1/36003 604/20 |
| 2016/0220813 A1 | 8/2016 | Edgerton et al. | |
| 2016/0235977 A1 | 8/2016 | Lu et al. | |
| 2017/0007831 A1 | 1/2017 | Edgerton et al. | |
| 2017/0157389 A1* | 6/2017 | Tai | A61N 1/0553 |
| 2017/0165497 A1 | 6/2017 | Lu | |
| 2017/0246450 A1 | 8/2017 | Liu et al. | |
| 2017/0246452 A1 | 8/2017 | Liu et al. | |
| 2017/0274209 A1 | 9/2017 | Edgerton et al. | |

FOREIGN PATENT DOCUMENTS

| | | |
|---|---|---|
| EP | 2661307 A2 | 11/2013 |
| EP | 2968940 A1 | 1/2016 |
| RU | 2130326 C1 | 5/1999 |
| RU | 2141851 C1 | 11/1999 |
| RU | 2160127 C1 | 12/2000 |
| RU | 2178319 C2 | 1/2002 |
| RU | 2192897 C2 | 11/2002 |
| RU | 2001102533 | 11/2002 |
| RU | 2226114 C1 | 3/2004 |
| RU | 2258496 C2 | 8/2005 |
| RU | 2361631 C2 | 7/2009 |
| RU | 2368401 C1 | 9/2009 |
| RU | 2387467 C1 | 4/2010 |
| RU | 2396995 C2 | 8/2010 |
| RU | 2397788 C2 | 8/2010 |
| RU | 2445990 C1 | 3/2012 |
| RU | 2471518 C2 | 1/2013 |
| RU | 2475283 C2 | 2/2013 |

(56) References Cited

FOREIGN PATENT DOCUMENTS

| WO | WO 97/047357 A1 | 12/1997 |
|---|---|---|
| WO | WO 03/026735 A2 | 4/2003 |
| WO | WO 03/092795 A1 | 11/2003 |
| WO | WO 2004/087116 A2 | 10/2004 |
| WO | WO 2005/051306 A2 | 6/2005 |
| WO | WO 2005/087307 A2 | 9/2005 |
| WO | WO 2007/107831 A2 | 9/2007 |
| WO | WO 2008/109862 A1 | 9/2008 |
| WO | WO 2008/121891 A1 | 10/2008 |
| WO | WO 2009/042217 A1 | 4/2009 |
| WO | WO 2009/111142 A2 | 9/2009 |
| WO | WO 2010/114998 A1 | 10/2010 |
| WO | WO 2010/124128 A1 | 10/2010 |
| WO | WO 2012/094346 A2 | 7/2012 |
| WO | WO 2012/100260 A2 | 7/2012 |
| WO | WO 2012/129574 A2 | 9/2012 |
| WO | WO 2013/071307 A1 | 5/2013 |
| WO | WO 2013/071309 A1 | 5/2013 |
| WO | WO 2014/144785 A1 | 9/2014 |
| WO | WO 2015/048563 A2 | 4/2015 |
| WO | WO 2016/029159 A2 | 2/2016 |
| WO | WO 2016/033369 A1 | 3/2016 |
| WO | WO 2016/033372 A1 | 3/2016 |
| WO | WO 2017/011410 A1 | 1/2017 |
| WO | WO 2017/024276 A1 | 2/2017 |
| WO | WO 2017/035512 A1 | 3/2017 |

OTHER PUBLICATIONS

U.S. Final Office Action dated Sep. 21, 2015 issued in U.S. Appl. No. 14/355,812.
U.S. Notice of Allowance dated Apr. 13, 2016 issued in U.S. Appl. No. 14/355,812.
U.S. Office Action dated Oct. 18, 2016 issued in U.S. Appl. No. 15/208,529.
PCT International Search Report dated Jul. 30, 2012 issued in PCT/US2012/020112.
PCT International Preliminary Report on Patentability and Written Opinion dated Jul. 10, 2013 issued in PCT/US2012/020112.
PCT International Search Report and Written Opinion dated Mar. 19, 2013 issued in PCT/US2012/064878.
PCT International Preliminary Report on Patentability dated May 22, 2014 issued in PCT/US2012/064878.
Australian Patent Examination Report No. 1 dated Jul. 11, 2016 issued in AU 2012334926.
European Communication pursuant to Rule 114(2) EPC regarding observations by a third party dated Mar. 27, 2015 issued in EP 12 847 885.6.
European Extended Search Report dated May 6, 2015 issued in EP 12 847 885.6.
European Office Action dated Apr. 15, 2016 issued in EP 12 847 885.6.
European Reply to Communication of Apr. 15, 2016 dated Oct. 24, 2016 in EP 12 847 885.6.
PCT Declaration of Non-Establishment of International Search Report and Written Opinion dated Dec. 24, 2014 issued in PCT/US2014/057886.
PCT International Preliminary Report on Patentability and Written Opinion dated Apr. 7, 2016 issued in PCT/US2014/057886.
PCT International Search Report and Written Opinion dated Aug. 6, 2014 issued in PCT/US2014/029340.
PCT International Preliminary Report on Patentability dated Sep. 24, 2015 issued in PCT/US2014/029340.
European Extended Search Report dated Nov. 8, 2016 issued in EP 14 76 5477.6.
PCT International Search Report and Written Opinion dated Dec. 5, 2016 issued in PCT/US2016/045898.
PCT International Search Report and Written Opinion dated Dec. 8, 2015 issued in PCT/US2015/047268.
PCT International Search Report and Written Opinion dated Dec. 3, 2015 issued in PCT/US2015/047272.
PCT Declaration of Non-Establishment of International Search Report and Written Opinion dated Dec. 1, 2015 issued in PCT/US2015/046378.
PCT International Search Report and Written Opinion dated Dec. 5, 2016 issued in PCT/US2016/049129.
PCT International Search Report dated Mar. 19, 2013 issued in PCT/US2012/064874.
PCT International Search Report dated Mar. 19, 2013 issued in PCT/US2012/064878.
PCT International Search Report dated Sep. 3, 2012 issued in PCT/US2012/022257.
PCT International Search Report dated Oct. 31, 2012 issued in PCT/US2012/030624.
Angeli et al. (2014) "Altering spinal cord excitability enables voluntary movements after chronic complete paralysis in humans" *Brain* 137: 1394-1409.
Courtine, Grégoire et al. (2007) "Modulation of multisegmental monosynaptic responses in a variety of leg muscles during walking and miming in humans," *J Physiol.* 582.3:1125-1139.
Danner S.M., Hofstoetter U.S., Ladenbauer J., Rattay F., and Minassian K. (Mar. 2011) "Can the human lumbar posterior columns be stimulated by transcutaneous spinal cord stimulation? A modeling study" *Europe PMC Flinders Author Manuscripts, Artif Organs* 35(3):257-262, 12 pp.
DeSantana et al. (Dec. 2008) "Effectiveness of Transcutaneous Electrical Nerve Stimulation for Treatment of Hyperalgesia and Pain," *Curr Rheumatol Rep.* 10(6):492-499, 12 pp.
Dubinsky, Richard M. and Miyasaki, Janis, "Assessment: Efficacy of transcutaneous electric nerve stimulation in the treatment of pain in neurologic disorders (an evidence-based review)," Report of the Therapeutics and Technology Assessment Subcommittee of the American Academy of Neurology, (2010) *Neurology*, 74:173-176.
Fong et al. (2009) "Recovery of control of posture and locomotion after a spinal cord injury: solutions staring us in the face," *Progress in Brain Research*, Elsevier Amsterdam, NL,175:393-418.
Ganley et al., (2005) "Epidural Spinal Cord Stimulation Improves Locomoter Performance in Low ASIA C, Wheelchair-Dependent, Spinal Cord-Injured Individuals: Insights from Metabolic Response," *Top. Spinal Cord Inj. Rehabil*;11(2):50-63.
Gerasimenko Y., Gorodnichev R., Machueva E., Pivovarova E., Semyenov D., Savochin A., Roy R.R., and Edgerton V.R., (Mar. 10, 2010) "Novel and Direct Access to the Human Locomotor Spinal Circuitry," *J Neurosci.* 30(10):3700-3708, PMC2847395.
Gerasimenko Y.P., Ichiyama R.M., Lavrov I.A., Courtine G., Cai L., Zhong H., Roy R.R., and Edgerton V.R. (2007) "Epidural Spinal Cord Stimulation Plus Quipazine Administration Enable Stepping in Complete Spinal Adult Rats," *J Neurophysiol.* 98:2525-2536.
Harkema et al. (2011) "Effect of Epidural stimulation of the lumbosacral spinal cord on voluntary movement, standing, and assisted stepping after motor complete paraplegia: a case study" *Lancet* 377(9781): 1938-1947; NIH Public Access Author Manuscript 17 pages [doi:10.1016/S0140-6736(11)60547-3].
Herman R., He J., D'Luzansky S., Willis W., Dilli S., (2002) "Spinal cord stimulation facilitates functional walking in a chronic, incomplete spinal cord injured," *Spinal Cord.* 40:65-68.
Hofstoetter, U.S. et al. (Aug. 2008) "Modification of Reflex Responses to Lumbar Posterior Root Stimulation by Motor Tasks in Healthy Subjects," *Artif Organs*, 32(8):644-648.
Ichiyama et al. (2005) "Hindlimb stepping movements in complete spinal rats induced by epidural spinal cord stimulation" *Neuroscience Letters*, 383:339-344.
Kitano K., Koceja D.M. (2009) "Spinal reflex in human lower leg muscles evoked by transcutaneous spinal cord stimulation," *J Neurosci Methods.* 180:111-115.
Minasian et al. (2010) "Transcutaneous stimulation of the human lumbar spinal cord: Facilitating locomotor output in spinal cord injury," *Conf. Proceedings Soc. for Neurosci.*, Abstract No. 286.19, 1 page.
Minassian et al. (Aug. 2011) "Transcutaneous spinal cord stimulation," *International Society for Restorative Neurology*, http://restorativeneurology.org/resource-center/assessments/transcutane-

(56) References Cited

OTHER PUBLICATIONS ous-lumbar-spinal-cord-stimulation/;http://restorativeneurology.org/wp-content/uploads/2011/08/Transcutaneous-spinal-cord-stimulation_long.pdf, 6 pp.

Minassian et al. (Mar. 2007) "Posterior root-muscle reflexes elicited by transcutaneous stimulation of the human lumbosacral cord," *Muscle & Nerve* 35:327-336.

Nandra et al., (2014) "Microelectrode Implants for Spinal Cord Stimulation in Rats," *Thesis, California Institute of Technology*, Pasadena, California, Defended on Sep. 24, 2014, 104 pages.

Nandra et al., (Jan. 23, 2011) "A Parylene-Based Microelectrode Arrray Implant for Spinal Cord Stimulation in Rats," *Conf. Proc. IEEE Eng. Med. Biol. Soc.*, pp. 1007-1010.

Rodger et al., (2007) "High Density Flexible Parylene-Based Multielectrode Arrays for Retinal and Spinal Cord Stimulation," Transducers & Eurosensors, Proc. of the 14th International Conference on Solid-State Sensors, Actuators and Microsystems, Lyon, France, Jun. 10-14, 2007, IEEE, pp. 1385-1388.

Seifert et al. (Nov. 1, 2002) "Restoration of Movement Using Functional Electrical Stimulation and Bayes' Theorem," *The Journal of Neuroscience*, 22(1):9465-9474.

Tanabe et al. (2008) "Effects of transcutaneous electrical stimulation combined with locomotion-like movement in the treatment of post-stroke gait disorder: a single-case study," 30(5):411-416 abstract, 1 page.

Ward, Alex R. (Feb. 2009) "Electrical Stimulation Using Kilohertz-Frequency Alternating Current ," (2009) *Phys Ther*.89(2):181-190 [published online Dec. 18, 2008].

U.S. Final Office Action dated Jul. 13, 2017 issued in U.S. Appl. No. 15/208,529.

U.S. Office Action dated Oct. 3, 2017 issued in U.S. Appl. No. 15/025,201.

European Second Office Action dated Feb. 16, 2017 issued in EP 12 847 885.6.

European Extended Search Report dated May 10, 2017 issued in EP 14849355.4.

PCT International Preliminary Report on Patentability and Written Opinion dated Feb. 28, 2017 issued in PCT/US2015/047268.

PCT International Preliminary Report on Patentability and Written Opinion dated Feb. 28, 2017 issued in PCT/US2015/047272.

PCT International Preliminary Report on Patentability and Written Opinion dated Feb. 21, 2017 issued in PCT/US2015/046378.

PCT International Search Report and Written Opinion dated Sep. 12, 2016 issued in PCT/US2016/041802.

\* cited by examiner

MULTI-SITE TRANSCUTANEOUS ELECTRICAL STIMULATION OF THE SPINAL CORD FOR FACILITATION OF LOCOMOTION

CROSS-REFERENCE TO RELATED APPLICATIONS

This application is a U.S. 371 National Phase of PCT/US2014/029340, filed on Mar. 14, 2014, which claims benefit of and priority to U.S. Ser. No. 61/802,034, filed Mar. 15, 2013, which is incorporated herein by reference in its entirety for all purposes.

STATEMENT OF GOVERNMENTAL SUPPORT

This invention was made with Government support under NS062009, awarded by the National Institutes of Health. The Government has certain rights in the invention.

FIELD

This application relates to the field of neurological treatment and rehabilitation for injury and disease including traumatic spinal cord injury, non-traumatic spinal cord injury, stroke, movement disorders, brain injury, ALS, Neurodegenerative Disorder, Dementia, Parkinson's disease, and other diseases or injuries that result in paralysis and/or nervous system disorder. Devices, pharmacological agents, and methods are provided to facilitate recovery of posture, locomotion, and voluntary movements of the arms, trunk, and legs, and recovery of autonomic, sexual, vasomotor, speech, swallowing, and respiration, in a human subject having spinal cord injury, brain injury, or any other neurological disorder.

BACKGROUND

Serious spinal cord injuries (SCI) affect approximately 1.3 million people in the United States, and roughly 12-15,000 new injuries occur each year. Of these injuries, approximately 50% are complete spinal cord injuries in which there is essentially total loss of sensory motor function below the level of the spinal lesion.

Neuronal networks formed by the interneurons of the spinal cord that are located in the cervical and lumbar enlargements, such as the spinal networks (SNs), can play an important role in the control of posture, locomotion and movements of the upper limbs, breathing and speech. Most researchers believe that all mammals, including humans, have SNs in the lumbosacral cord. Normally, the activity of SNs is regulated supraspinally and by peripheral sensory input. In the case of disorders of the connections between the brain and spinal cord, e.g., as a result of traumatic spinal cord lesions, motor tasks can be enabled by epidural electrical stimulation of the lumbosacral and cervical segments as well as the brainstem.

SUMMARY

We have demonstrated that enablement of motor function can be obtained as well with the use of non-invasive external spinal cord electrical stimulation.

Various embodiments described herein are for use with a mammal including (e.g., a human or a non-human mammal) who has a spinal cord with at least one selected dysfunctional spinal circuit or other neurologically derived source of control of movement or function in a portion of the subject's body. Transcutaneous electrical spinal cord stimulation (tESCS) can be applied in the regions of the C4-C5, T11-T12 and/or L1-L2 vertebrae with a frequency of 5-40 Hz. Such stimulation can elicit involuntary step-like movements in healthy subjects with their legs suspended in a gravity-neutral position. By way of non-limiting examples, application of transcutaneous electrical spinal cord stimulation (tESCS) at multiple sites on the subject's spinal cord is believed to activate spinal locomotor networks (SNs), in part via the dorsal roots and the gray matter of the spinal cord. When activated, the SNs may, inter alia (a) enable voluntary movement of muscles involved in at least one of standing, stepping, reaching, grasping, voluntarily changing positions of one or both legs, breathing, speech control, swallowing, voiding the patient's bladder, voiding the patient's bowel, postural activity, and locomotor activity; (b) enable or improve autonomic control of at least one of cardiovascular function, body temperature, and metabolic processes; and/or (c) help facilitate recovery of at least one of an autonomic function, sexual function, or vasomotor function. According to some embodiments, the present disclosure provides that the spinal circuitry is neuromodulated to a physiological state that facilitates or enables the recovery or improved control of movement and function following some neuromotor dysfunction.

The paralysis may be a motor complete paralysis or a motor incomplete paralysis. The paralysis may have been caused by a spinal cord injury classified as motor complete or motor incomplete. The paralysis may have been caused by an ischemic or traumatic brain injury. The paralysis may have been caused by an ischemic brain injury that resulted from a stroke or acute trauma. By way of another example, the paralysis may have been caused by a neurodegenerative condition affecting the brain and/or spinal cord. The neurodegenerative brain injury may be associated with at least one of Parkinson's disease, Huntington's disease, Alzheimer's, Frontotemporal Dementia, dystonia, ischemic stroke, amyotrophic lateral sclerosis (ALS), primary lateral sclerosis (PLS), and other conditions such as cerebral palsy and Multiple Sclerosis.

By way of non-limiting example, a method includes applying electrical stimulation to a portion of a spinal cord or brainstem of the subject. The electrical stimulation may be applied by (or through) a surface electrode(s) that is applied to the skin surface of the subject. Such an electrode may be positioned at, at least one of a thoracic region, a cervical region, a thoraco-lumbar region, a lumbosacral region of the spinal cord, the brainstem and/or a combination thereof. In certain embodiments the electrical stimulation is delivered at 5-40 Hz at 20-100 mA. While not a requirement, the electrical stimulation may not directly activate muscle cells in the portion of the patient's body having the paralysis. The electrical stimulation may include at least one of tonic stimulation and intermittent stimulation. The electrical stimulation may include simultaneous or sequential stimulation of different regions of the spinal cord.

If the paralysis was caused by a spinal cord injury at a first location along the spinal cord, the electrical stimulation may be applied by an electrode that is on the spinal cord of the patient at a second location below the first location along the spinal cord relative to the patient's brain.

Optionally, the method may include administering one or more neuropharmaceutical agents to the patient. The neuropharmaceutical agents may include at least one of a serotonergic drug, a dopaminergic drug, a noradrenergic drug, a GABAergic drug, and glycinergic drugs. By way of non-limiting examples, the neuropharmaceutical agents may include at least one of 8-OHDPAT, Way 100.635, Quipazine, Ketanserin, SR 57227A, Ondanesetron, SB 269970, Buspirone, Methoxamine, Prazosin, Clonidine, Yohimbine, SKF-81297, SCH-23390, Quinpirole, and Eticlopride.

The electrical stimulation is defined by a set of parameter values, and activation of the selected spinal circuit may generate a quantifiable result. Optionally, the method may be repeated using electrical stimulation having different sets of parameter values to obtain quantifiable results generated by each repetition of the method. Then, a machine learning method may be executed by at least one computing device. The machine learning method builds a model of a relationship between the electrical stimulation applied to the spinal cord and the quantifiable results generated by activation of the at least one spinal circuit. A new set of parameters may be selected based on the model. By way of a non-limiting example, the machine learning method may implement a Gaussian Process Optimization.

Another illustrative embodiment is a method of enabling one or more functions selected from a group consisting of postural and/or locomotor activity, voluntary movement of leg position when not bearing weight, improved breathing and ventilation, speech control, swallowing, voluntary voiding of the bladder and/or bowel, return of sexual function, autonomic control of cardiovascular function, body temperature control, and normalized metabolic processes, in a human subject having a neurologically derived paralysis. The method includes stimulating the spinal cord of the subject using a surface electrode while subjecting the subject to physical training that exposes the subject to relevant postural proprioceptive signals, locomotor proprioceptive signals, and supraspinal signals. At least one of the stimulation and physical training modulates in real time provoke or incite the electrophysiological properties of spinal circuits in the subject so the spinal circuits are activated by at least one of supraspinal information and proprioceptive information derived from the region of the subject where the selected one or more functions are facilitated.

The region where the selected one or more functions are facilitated may include one or more regions of the spinal cord that control (a) lower limbs; (b) upper limbs and brainstem for controlling speech; (c) the subject's bladder; (d) the subject's bowel and/or other end organ. The physical training may include, but need not be limited to, standing, stepping, sitting down, laying down, reaching, grasping, stabilizing sitting posture, and/or stabilizing standing posture. It is also contemplated that in certain embodiments, the physical training can include, but need not be limited to swallowing, chewing, grimacing, shoulder shrugging, and the like.

The surface electrode may include single electrode(s) or one or more arrays of one or more electrodes stimulated in a monopolar biphasic configuration, a monopolar monophasic configuration, or a bipolar biphasic or monophasic configuration. Such a surface electrode may be placed over at least one of all or a portion of a lumbosacral portion of the spinal cord, all or a portion of a thoracic portion of the spinal cord, all or a portion of a cervical portion of the spinal cord, the brainstem or a combination thereof.

The stimulation may include tonic stimulation and/or intermittent stimulation. The stimulation may include simultaneous or sequential stimulation, or combinations thereof, of different spinal cord regions. Optionally, the stimulation pattern may be under control of the subject.

The physical training may include inducing a load bearing positional change in the region of the subject where locomotor activity is to be facilitated. The load bearing positional change in the subject may include standing, stepping, reaching, and/or grasping. The physical training may include robotically guided training.

The method may also include administering one or more neuropharmaceuticals. The neuropharmaceuticals may include at least one of a serotonergic drug, a dopaminergic drug, a noradrenergic drug, a GABAergic drug, and a glycinergic drug.

Another illustrative embodiment is a method that includes placing an electrode on the patient's spinal cord, positioning the patient in a training device configured to assist with physical training that is configured to induce neurological signals in the portion of the patient's body having the paralysis, and applying electrical stimulation to a portion of a spinal cord of the patient, such as a biphasic signal of 30-40 Hz at 85-100 mA.

Another illustrative embodiment is a system that includes a training device configured to assist with physically training of the patient, a surface electrode array configured to be applied on the patient's spinal cord, and a stimulation generator connected to the electrode. When undertaken, the physical training induces neurological signals in the portion of the patient's body having the paralysis. The stimulation generator is configured to apply electrical stimulation to the electrode. Electrophysiological properties of at least one spinal circuit in the patient's spinal cord is modulated by the electrical stimulation and at least one of (1) a first portion of the induced neurological signals and (2) supraspinal signals such that the at least one spinal circuit is at least partially activatable by at least one of (a) the supraspinal signals and (b) a second portion of the induced neurological signals.

Definitions

The term "motor complete" when used with respect to a spinal cord injury indicates that there is no motor function below the lesion, (e.g., no movement can be voluntarily induced in muscles innervated by spinal segments below the spinal lesion.

As used herein "electrical stimulation" or "stimulation" means application of an electrical signal that may be either excitatory or inhibitory to a muscle or neuron. It will be understood that an electrical signal may be applied to one or more electrodes with one or more return electrodes.

The term "monopolar stimulation" refers to stimulation between a local electrode and a common distant return electrode.

As used herein "epidural" means situated upon the dura or in very close proximity to the dura. The term "epidural stimulation" refers to electrical epidural stimulation. In certain embodiments epidural stimulation is referred to as "electrical enabling motor control" (eEmc).

The term "transcutaneous stimulation" or "transcutaneous electrical stimulation" or "cutaneous electrical stimulation" refers to electrical stimulation applied to the skin, and, as typically used herein refers to electrical stimulation applied to the skin in order to effect stimulation of the spinal cord or a region thereof. The term "transcutaneous electrical spinal cord stimulation" may also be referred to as "tSCS".

The term "autonomic function" refers to functions controlled by the peripheral nervous system that are controlled largely below the level of consciousness, and typically involve visceral functions. Illustrative autonomic functions include, but are not limited to control of bowel, bladder, and body temperature.

The term "sexual function" refers to the ability to sustain a penile erection, have an orgasm (male or female), generate viable sperm, and/or undergo an observable physiological change associated with sexual arousal.

The term "co-administering", "concurrent administration", "administering in conjunction with" or "administering in combination" when used, for example with respect to transcutaneous electrical stimulation, epidural electrical stimulation, and pharmaceutical administration, refers to administration of the transcutaneous electrical stimulation and/or epidural electrical stimulation and/or pharmaceutical such that various modalities can simultaneously achieve a physiological effect on the subject. The administered modalities need not be administered together, either temporally or at the same site. In some embodiments, the various "treatment" modalities are administered at different times. In some embodiments, administration of one can precede administration of the other (e.g., drug before electrical stimulation or vice versa). Simultaneous physiological effect need not necessarily require presence of drug and the electrical stimulation at the same time or the presence of both stimulation modalities at the same time. In some embodiments, all the modalities are administered essentially simultaneously.

BRIEF DESCRIPTION OF THE DRAWINGS

FIG. 5 shows angular movements of the right (R) knee and left (L) knee joints and representative EMG activity in the rectus femoris (RF), biceps femoris (BF) tibialis anterior (TA) and medial gastrocnemius (MG) muscles during involuntary locomotor-like activity induced by transcutaneous spinal cord stimulation at the T11 vertebra at 5 and 30 Hz. FIG. 5B shows stick diagram decompositions (40 ms between sticks) of the movements of the R leg and trajectory of toe movements during one step cycle during PTES at T11-T12. Arrows in FIG. 5B indicate the direction of movement.

DETAILED DESCRIPTION

Figure 1:
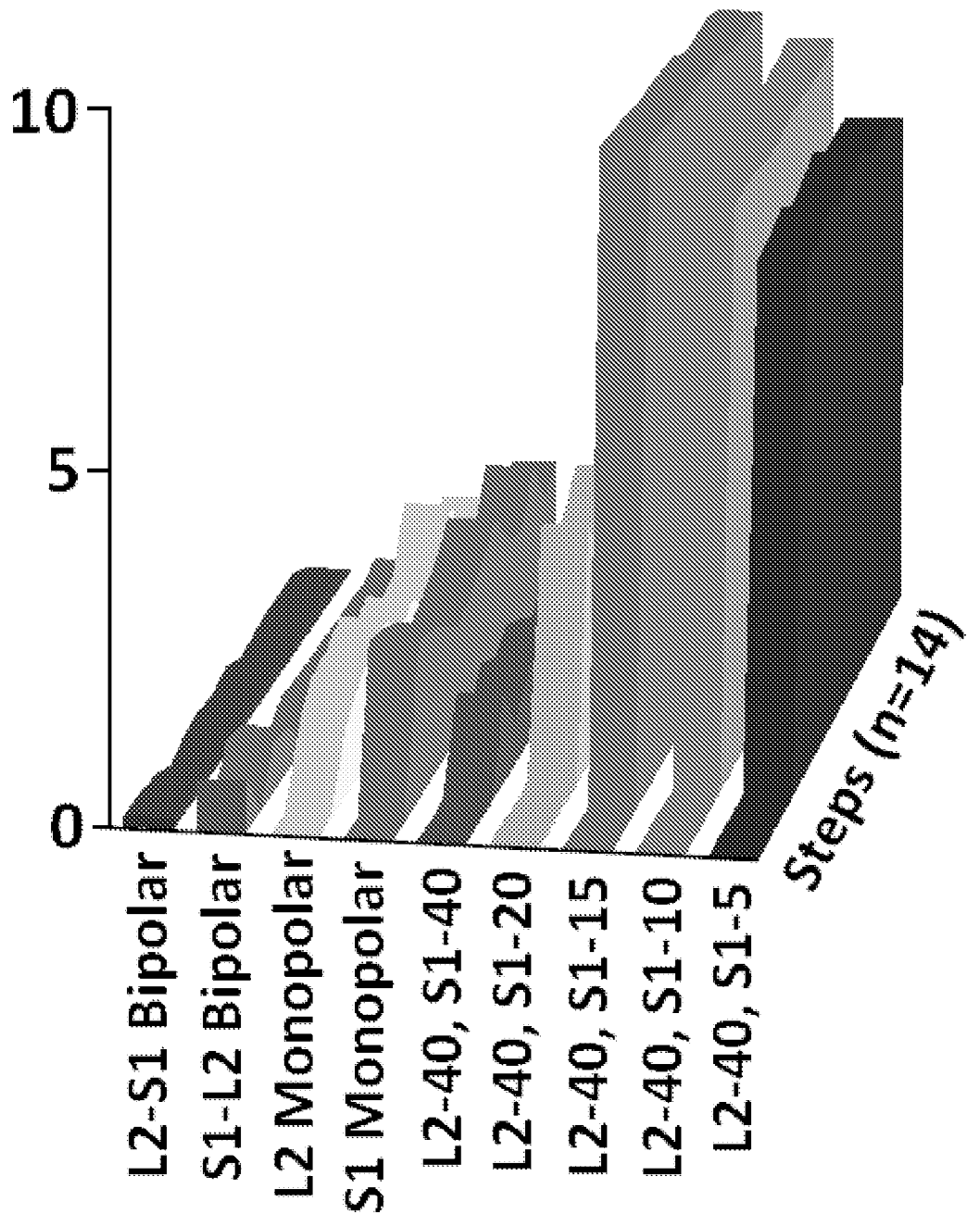
FIG. 1 is an example embodiment illustrating peak EMG amplitudes in the vastus lateralis in response to epidural stimulation at L2 and/or S1 spinal segments using nine combinations.

Disclosed herein are methods for inducing locomotor activity in a mammal. These methods can comprise administering epidural or transcutaneous electrical spinal cord stimulation (tSCS) to the mammal at a frequency and intensity that induces the locomotor activity.

It is demonstrated herein in spinal rats (motor complete rats) and non-injured human subjects that simultaneous spinal cord stimulation at multiple sites has an interactive effect on the spinal neural circuitries responsible for generating locomotion. In particular, it was discovered inter alia, that simultaneous multisite epidural stimulation with specific parameters allows for a more precise control of these postural-locomotor interactions, resulting in robust, coordinated plantar full weight-bearing stepping in complete spinal rats. The EMG stepping pattern during simultaneous multi-site epidural stimulation was significantly improved compared to certain bipolar stimulation configurations (e.g., between L2 and S1) or certain monopolar stimulation configurations (e.g., at L2 or S1). Without being bound to a particular theory it is believed that one added benefit of second-site (e.g., S1 added to L2) stimulation with specific parameters may be related to activation of postural neuronal circuitries and activation of rostrally projecting propriospinal neurons from the more caudal segments that contribute to the rhythm and pattern of output of the locomotor circuitry.

It is also demonstrated herein using transcutaneous spinal cord stimulation in non-injured humans that the lumbosacral locomotor circuitry can be accessed using a non-invasive pain free procedure. In an illustrative, but non-limiting embodiment, it is shown that transcutaneous spinal cord stimulation applied to stimulation at the L2 spinal segment (T11-T12 vertebral level) is able to activate this locomotor circuitry. It is believed the results demonstrated herein provide the first example of using multi-segmental non-invasive electrical spinal cord stimulation to facilitate involuntary, coordinated stepping movements.

Without being bound by a particular theory, it is believed that the synergistic and interactive effects of multi-level stimulation in both the animal and human studies indicates a multi-segmental convergence of descending and ascending, and most likely propriospinal, influences on the spinal neuronal circuitries associated with locomotor and postural activity.

Accordingly, in some embodiments, the electrical spinal cord stimulation is applied at two spinal levels simultaneously. In other embodiments, the electrical spinal cord stimulation is applied at three spinal levels simultaneously. In still over embodiments the electrical spinal cord stimulation is at four spinal levels simultaneously. The spinal levels can be the cervical, thoracic, lumbar, sacral, or a combination thereof. In certain embodiments the spinal levels can be the cervical, thoracic, lumbar, or a combination thereof.

In certain embodiments, the stimulation can be to a brain stem and/or cervical level. In some embodiments, the brainstem/cervical level can be a region over at least one C0-C7 or C1-C7, over at least two of C0-C7 or C1-C7, over at least three of C0-C7 or C1-C7, over at least four of C0-C7 or C1-C7, over at least five of C0-C7 or C1-C7, over at least six of C0-C7 or C1-C7, over C1-C7, over C4-C5, over C3-C5, over C4-C6, over C3-C6, over C2-C5, over C3-C7, or over C3 to C7.

Additionally or alternatively, the stimulation can be to a thoracic level. In some embodiments, the thoracic level can be a region over at least one of T1 to T12, at least two of T1 to T12, at least three of T1 to T12, at least four of T1 to T12, at least five of T1 to T12, at least six of T1 to T12, at least seven of T1 to T12, at least 8 of T1 to T12, at least 9 of T1 to T12, at least 10 of T1 to T12, at least 11 of T1 to T12, T1 to T12, over T1 to T6, or over a region of T11-T12, T10-T12, T9-T12, T8-T12, T8-T11, T8 to T10, T8 to T9, T9-T12, T9-T11, T9-T10, or T11-T12.

Additionally or alternatively, the stimulation can be to a lumbar level. In some embodiments, the lumbar level can be a region over at least one of L1-L5, over at least two of L1-L5, over at least three of L1-L5, over at least four of L1-L5, or L1-L5.

Additionally or alternatively, the stimulation can be to a sacral level. In some embodiments, the sacral level can be a region over at least one S1-S5, over at least two of S1-S5, over late least three of S1-S5, over at least four of S1-S5, or over S1-S5. In certain embodiments, the stimulation is over a region including S1. In certain embodiments, the stimulation over a sacral level is over S1.

In some embodiments, the transcutaneous electrical spinal cord stimulation is applied paraspinally over regions that include, but need not be limited to C4-C5, T11-T12, and/or L1-L2 vertebrae. In some embodiments, the transcutaneous electrical spinal cord stimulation is applied paraspinally over regions that consist of regions over C4-C5, T11-T12, and/or L1-L2 vertebrae.

In various embodiments, the transcutaneous stimulation can be applied at an intensity ranging from about 30 to 200 mA, about 110 to 180 mA, about 10 mA to about 150 mA, from about 20 mA to about 100 mA, or from about 30 or 40 mA to about 70 mA or 80 mA.

In various embodiments the transcutaneous stimulation can be applied at a frequency ranging from about 1 Hz to about 100 Hz, from about 5 Hz to about 80 Hz, or from about 5 Hz to about 30 Hz, or about 40 Hz, or about 50 Hz.

As demonstrated herein, non-invasive transcutaneous electrical spinal cord stimulation (tSCS) can induce locomotor-like activity in non-injured humans. Continuous tSCS (e.g., at 5-40 Hz) applied paraspinally over the T11-T12 vertebrae can induce involuntary stepping movements in subjects with their legs in a gravity-independent position. These stepping movements can be enhanced when the spinal cord is stimulated at two to three spinal levels (C5, T12, and/or L2) simultaneously with frequency in the range of 5-40 Hz. Further, locomotion of spinal animals can be improved, in some embodiments substantially, when locomotor and postural spinal neuronal circuitries are stimulated simultaneously.

In some embodiments, epidural spinal cord stimulation can be applied independently at the L2 and at the S1 spinal segments to facilitate locomotion as demonstrated herein in complete spinal adult rats. Simultaneous epidural stimulation at L2 (40 Hz) and at S1 (10-20 Hz) can enable full weight-bearing plantar hindlimb stepping in spinal rats. Stimulation at L2 or S1 alone can induce rhythmic activity, but, in some embodiments, with minimal weight bearing. In non-injured human subjects with the lower limbs placed in a gravity-neutral position, transcutaneous electrical stimulation (5 Hz) delivered simultaneously at the C5, T11, and L2 vertebral levels facilitated involuntary stepping movements that were significantly stronger than stimulation at T11 alone. Accordingly, simultaneous spinal cord stimulation at multiple sites can have an interactive effect on the spinal circuitry responsible for generating locomotion.

By non-limiting example, transcutaneous electrical stimulation can be applied to facilitate restoration of locomotion and other neurologic function in subjects suffering with spinal cord injury, as well as other neurological injury and illness. Successful application can provide a device for widespread use in rehabilitation of neurologic injury and disease.

In embodiments, methods, devices, and optional pharmacological agents are provided to facilitate movement in a mammalian subject (e.g., a human) having a spinal cord injury, brain injury, or other neurological disease or injury. In some embodiments, the methods can involve stimulating the spinal cord of the subject using a surface electrode where the stimulation modulates the electrophysiological properties of selected spinal circuits in the subject so they can be activated by proprioceptive derived information and/or input from supraspinal. In various embodiments, the stimulation may be accompanied by physical training (e.g., movement) of the region where the sensory-motor circuits of the spinal cord are located.

In some embodiments, the devices, optional pharmacological agents, and methods described herein stimulate the spinal cord with, e.g., electrodes that modulate the proprioceptive and supraspinal information which controls the lower limbs during standing and/or stepping and/or the upper limbs during reaching and/or grasping conditions. It is the proprioceptive and cutaneous sensory information that guides the activation of the muscles in a coordinated manner and in a manner that accommodates the external conditions, e.g., the amount of loading, speed, and direction of stepping or whether the load is equally dispersed on the two lower limbs, indicating a standing event, alternating loading indicating stepping, or sensing postural adjustments signifying the intent to reach and grasp.

Unlike approaches that involve specific stimulation of motor neurons to directly induce a movement, the methods described herein enable the spinal circuitry to control the movements. More specifically, the devices, optional pharmacological agents, and methods described herein can exploit the spinal circuitry and its ability to interpret proprioceptive information and to respond to that proprioceptive information in a functional way. In various embodiments, this is in contrast to other approaches where the actual movement is induced/controlled by direct stimulation (e.g., of particular motor neurons).

In one embodiment, the subject is fitted with one or more surface electrodes that afford selective stimulation and control capability to select sites, mode(s), and intensity of stimulation via electrodes placed superficially over, for example, the lumbosacral spinal cord and/or the thoracic spinal cord, and/or the cervical spinal cord to facilitate movement of the arms and/or legs of individuals with a severely debilitating neuromotor disorder.

In some embodiments, the subject is provided a generator control unit and is fitted with an electrode(s) and then tested to identify the most effective subject specific stimulation paradigms for facilitation of movement (e.g., stepping and standing and/or arm and/or hand movement). Using the herein described stimulation paradigms, the subject practices standing, stepping, reaching, grabbing, breathing, and/or speech therapy in an interactive rehabilitation program while being subject to spinal stimulation.

Depending on the site/type of injury and the locomotor activity it is desired to facilitate, particular spinal stimulation protocols include, but are not limited to, specific stimulation sites along the lumbosacral, thoracic, cervical spinal cord or a combination thereof; specific combinations of stimulation sites along the lumbosacral, thoracic, cervical spinal cord and/or a combination thereof; specific stimulation amplitudes; specific stimulation polarities (e.g., monopolar and bipolar stimulation modalities); specific stimulation frequencies; and/or specific stimulation pulse widths.

In various embodiments, the system is designed so that the patient can use and control in the home environment.

In various embodiments, the electrodes of electrode arrays are operably linked to control circuitry that permits selection of electrode(s) to activate/stimulate and/or that controls frequency, and/or pulse width, and/or amplitude of stimulation. In various embodiments, the electrode selection, frequency, amplitude, and pulse width are independently selectable, e.g., at different times, different electrodes can be selected. At any time, different electrodes can provide different stimulation frequencies and/or amplitudes. In various embodiments, different electrodes or all electrodes can be operated in a monopolar mode and/or a bipolar mode, using e.g., constant current or constant voltage delivery of the stimulation.

In one illustrative but non-limiting system a control module is operably coupled to a signal generation module and instructs the signal generation module regarding the signal to be generated. For example, at any given time or period of time, the control module may instruct the signal generation module to generate an electrical signal having a specified pulse width, frequency, intensity (current or voltage), etc. The control module may be preprogrammed prior to use or receive instructions from a programmer (or another source). Thus, in certain embodiments the pulse generator/controller is configurable by software and the control parameters may be programmed/entered locally, or downloaded as appropriate/necessary from a remote site.

In certain embodiments the pulse generator/controller may include or be operably coupled to memory to store instructions for controlling the stimulation signal(s) and may contain a processor for controlling which instructions to send for signal generation and the timing of the instructions to be sent.

While in certain embodiments, two leads are utilized to provide transcutaneous stimulation, it will be understood that any number of one or more leads may be employed. In addition, it will be understood that any number of one or more electrodes per lead may be employed. Stimulation pulses are applied to electrodes (which typically are cathodes) with respect to a return electrode (which typically is an anode) to induce a desired area of excitation of electrically excitable tissue in one or more regions of the spine. A return electrode such as a ground or other reference electrode can be located on same lead as a stimulation electrode. However, it will be understood that a return electrode may be located at nearly any location, whether in proximity to the stimulation electrode or at a more remote part of the body, such as at a metallic case of a pulse generator. It will be further understood that any number of one or more return electrodes may be employed. For example, there can be a respective return electrode for each cathode such that a distinct cathode/anode pair is formed for each cathode.

In various embodiments, the approach is not to electrically induce a walking pattern or standing pattern of activation, but to enable/facilitate it so that when the subject manipulates their body position, the spinal cord can receive proprioceptive information from the legs (or arms) that can be readily recognized by the spinal circuitry. Then, the spinal cord knows whether to step or to stand or to do nothing. In other words, this enables the subject to begin stepping or to stand or to reach and grasp when they choose after the stimulation pattern has been initiated.

Moreover, the methods and devices described herein are effective in a spinal cord injured subject that is clinically classified as motor complete; that is, there is no motor function below the lesion; however the approach is not limited and may be used in subjects classified as motor-incomplete. In various embodiments, the specific combination of electrode(s) activated/stimulated and/or the desired stimulation of any one or more electrodes and/or the stimulation amplitude (strength) can be varied in real time, e.g., by the subject. Closed loop control can be embedded in the process by engaging the spinal circuitry as a source of feedback and feedforward processing of proprioceptive input and by voluntarily imposing fine tuning modulation in stimulation parameters based on visual, and/or kinetic, and/or kinematic input from selected body segments.

In various embodiments, the devices, optional pharmacological agents, and methods are designed so that a subject with no voluntary movement capacity can execute effective standing and/or stepping and/or reaching and/or grasping. In addition, the approach described herein can play an important role in facilitating recovery of individuals with severe although not complete injuries.

The approach described herein can provide some basic postural, locomotor and reaching and grasping patterns on their own. However, in some embodiments, the methods described herein can also serve as building blocks for future recovery strategies. In other embodiments, combining transcutaneous stimulation of appropriate spinal circuits with physical rehabilitation and pharmacological intervention can provide practical therapies for complete SCI human patients. The methods described herein can be sufficient to enable weight bearing standing, stepping and/or reaching or grasping in SCI patients. Such capability can give SCI patients with complete paralysis or other neuromotor dysfunctions the ability to participate in exercise, which can be beneficial, if not highly beneficial, for their physical and mental health.

In other embodiments, the methods described herein can enable movement with the aid of assistive walkers. In some embodiments, simple standing and short duration walking can increase these patients' autonomy and quality of life. The stimulating technology described herein (e.g., transcutaneous electrical spinal cord stimulation) can provide a direct brain-to-spinal cord interface that can enable more lengthy and finer control of movements.

While the methods and devices described herein are discussed with reference to complete spinal injury, it will be recognized that they can apply to subjects with partial spinal injury, subjects with brain injuries (e.g., ischemia, traumatic brain injury, stroke, and the like), and/or subjects with neurodegenerative diseases (e.g., Parkinson's disease, Alzheimer's disease, Huntington's disease, amyotrophic lateral sclerosis (ALS), primary lateral sclerosis (PLS), cerebral palsy, dystonia, and the like).

In various embodiments, the methods combine the use of transcutaneous stimulating electrode(s) with physical training (e.g., rigorously monitored (robotic) physical training), optionally in combination with pharmacological techniques. The methods enable the spinal cord circuitry to utilize sensory input as well as newly established functional connections from the brain to circuits below the spinal lesion as a source of control signals. The herein described methods can enable and facilitate the natural sensory input as well as supraspinal connections to the spinal cord in order to control movements, rather than induce the spinal cord to directly induce the movement. That is, the presently described methods can facilitate and enhance intrinsic neural control mechanisms of the spinal cord that exist post-SCI, rather than replace or ignore them.

Processing of Sensory Input by the Spinal Cord: Using Afferents as a Source of Control In various embodiments the methods and devices described herein can exploit spinal control of locomotor activity. For example, the human spinal cord can receive sensory input associated with a movement such as stepping, and this sensory information can be used to modulate the motor output to accommodate the appropriate speed of stepping and level of load that is imposed on lower limbs. In some embodiments, the present methods can utilize the central-pattern-generation-like properties of the human spinal cord (e.g., the lumbosacral spinal cord). Thus, for example, exploiting inter alia the central-pattern-generation-like properietes of the lumbosacral spinal cord, oscillations of the lower limbs can be induced simply by vibrating the vastus lateralis muscle of the lower limb, by transcutaneous stimulation, and by stretching the hip. The methods described herein exploit the fact that the human spinal cord, in complete or incomplete SCI subjects, can receive and interpret proprioceptive and somatosensory information that can be used to control the patterns of neuromuscular activity among the motor pools necessary to generate particular movements, e.g., standing, stepping, reaching, grasping, and the like.

Moreover, in certain embodiments, the methods described herein exploit the fact that stimulation (e.g., transcutaneous stimulation) of multiple levels can improve the ability of the spinal cord in complete or incomplete SCI subjects to receive and interpret proprioceptive and somatosensory information that can be used to control the patterns of neuromuscular activity among the motor pools necessary to generate particular movements In various embodiments, The methods described herein can facilitate and adapt the operation of the existing spinal circuitry that generates, for example, cyclic step-like movements via a combined approach of transcutaneous stimulation, physical training, and, optionally, pharmacology.

Facilitating Stepping and Standing in Humans Following a Clinically Complete Lesion In various embodiments, the methods described herein can comprise stimulation of one or more regions of the spinal cord in combination with locomotory activities. In other embodiments, spinal stimulation can be combined with locomotor activity thereby providing modulation of the electrophysiological properties of spinal circuits in the subject so they are activated by proprioceptive information derived from the region of the subject where locomotor activity is to be facilitated. Further, spinal stimulation in combination with pharmacological agents and locomotor activity may result in the modulation of the electrophysiological properties of spinal circuits in the subject so they are activated by proprioceptive information derived from the region of the subject where locomotor activity is to be facilitated.

In certain embodiments of the presently described methods, locomotor activity of the region of interest can be assisted or accompanied by any of a number of methods known, for example, to physical therapists. By way of illustration, individuals after severe SCI can generate standing and stepping patterns when provided with body weight support on a treadmill and manual assistance. During both stand and step training of human subjects with SCI, the subjects can be placed on a treadmill in an upright position and suspended in a harness at the maximum load at which knee buckling and trunk collapse can be avoided. Trainers positioned, for example, behind the subject and at each leg assist as needed in maintaining proper limb kinematics and kinetics appropriate for each specific task. During bilateral standing, both legs can be loaded simultaneously and extension can be the predominant muscular activation pattern, although co-activation of flexors can also occur. Additionally, or alternatively, during stepping the legs can be loaded in an alternating pattern and extensor and flexor activation patterns within each limb also alternated as the legs moved from stance through swing. Afferent input related to loading and stepping rate can influence these patterns, and training has been shown to improve these patterns and function in clinically complete SCI subjects.

Transcutaneous Electrical Stimulation of the Spinal Cord

As indicated above, without being bound by a particular theory, it is believed that transcutaneous electrical stimulation, e.g., over one spinal level, over two spinal levels simultaneously, or over three spinal levels simultaneously, in combination with physical training can facilitate recovery of stepping and standing in human subjects following a complete SCI.

In some embodiments, the location of electrode(s) and the stimulation parameters may be important in defining the motor response. In other embodiments, the use of surface electrode(s), as described herein, facilitates selection or alteration of particular stimulation sites as well as the application of a wide variety of stimulation parameters.

Use of Neuromodulatory Agents

In certain embodiments, the transcutaneous and/or epidural stimulation methods described herein are used in conjunction with various pharmacological agents, particularly pharmacological agents that have neuromodulatory activity (e.g., are monoamergic). In certain embodiments, the use of various serotonergic, and/or dopaminergic, and/or noradrenergic and/or GABAergic, and/or glycinergic drugs is contemplated. These agents can be used in conjunction with the stimulation and/or physical therapy as described above. This combined approach can help to put the spinal cord (e.g., the cervical spinal cord) in an optimal physiological state for controlling a range of hand movements.

In certain embodiments, the drugs are administered systemically, while in other embodiments, the drugs are administered locally, e.g., to particular regions of the spinal cord. Drugs that modulate the excitability of the spinal neuromotor networks include, but are not limited to combinations of noradrenergic, serotonergic, GABAergic, and glycinergic receptor agonists and antagonists. Illustrative pharmacological agents include, but are not limited to. agonists and antagonists to one or more combinations of serotonergic: 5-HT1A, 5-HT2A, 5-HT3, and 5HT7 receptors; to noradrenergic alpha1 and 2 receptors; and to dopaminergic D1 and D2 receptors (see, e.g., Table 1).

TABLE 1

Illustrative pharmacological agents.

| Name | Target | Action | Route | Typical Dose (mg/Kg) | Typical Range (mg/kg) |
|---|---|---|---|---|---|
| Serotonergic receptor systems | | | | | |
| 8-OHDPAT | 5-HT1A7 | Agonist | S.C. | 0.05 | 0.045-0.3 |
| Way 100.635 | 5-HT1A | Antagonist | I.P. | 0.5 | 0.4-1.5 |
| Quipazine | 5-HT2A/C | Agonist | I.P. | 0.2 | 0.18-0.6 |
| Ketanserin | 5-HT2A/C | Antagonist | I.P. | 3 | 1.5-6.0 |
| SR 57227A | 5-HT3 | Agonist | I.P. | 1.5 | 1.3-1.7 |
| Ondanesetron | 5-HT3 | Antagonist | I.P. | 3 | 1.4-7.0 |
| SB269970 | 5-HT7 | Antagonist | I.P. | 7 | 2.0-10.0 |
| Noradrenergic receptor systems | | | | | |
| Methoxamine | Alpha1 | Agonist | I.P. | 2.5 | 1.5-4.5 |
| Prazosin | Alpha1 | Antagonist | I.P. | 3 | 1.8-3.0 |
| Clonidine | Alpha2 | Agonist | I.P. | 0.5 | 0.2-1.5 |
| Yohimbine | Alpha2 | Antagonist | I.P. | 0.4 | 0.3-0.6 |
| Dopaminergic receptor systems | | | | | |
| SKF-81297 | D1-like | Agonist | I.P. | 0.2 | 0.15-0.6 |
| SCH-23390 | D1-like | Antagonist | I.P. | 0.15 | 0.1-0.75 |
| Quinipirole | D2-like | Agonist | I.P. | 0.3 | 0.15-0.3 |
| Eticlopride | D2-like | Antagonist | I.P. | 1.8 | 0.9-1.8 |

The foregoing methods are intended to be illustrative and non-limiting. Using the teachings provided herein, other methods involving transcutaneous electrical stimulation and/or epidural electrical stimulation and/or the use of neuromodulatory agents to improve motor control and/or strength of a hand or paw will be available to one of skill in the art.

In various aspects, the invention(s) contemplated herein may include, but need not be limited to, any one or more of the following embodiments:

Embodiment 1

A method of inducing locomotor activity in a mammal, said method including administering transcutaneous electrical spinal cord stimulation (tSCS) to said mammal at a frequency and intensity that induces said locomotor activity.

Embodiment 2

The method of embodiment 1, wherein said mammal is a human.

Embodiment 3

The method of embodiment 2, wherein said electrical spinal cord stimulation is applied at two spinal levels simultaneously.

Embodiment 4

The method of embodiment 3, wherein said two spinal levels are selected from cervical thoracic, lumbar or combinations thereof.

Embodiment 5

The method of embodiment 4, wherein said two spinal levels include cervical and thoracic.

Embodiment 6

The method of embodiment 4, wherein said two spinal levels include cervical and lumbar.

Embodiment 7

The method of embodiment 4, wherein said two spinal levels include thoracic and lumbar.

Embodiment 8

The method of embodiment 2, wherein said electrical spinal cord stimulation is applied at three spinal levels simultaneously.

Embodiment 9

The method according to any one of embodiments 3-8, wherein stimulation to a cervical level is to a region over at least one C1-C7, over at least two of C1-C7, over late least three of C1-C7, over at least four of C1-C7, over at least five of C1-C7, over at least six of C1-C7, or over C1-C7.

Embodiment 10

The method according to any one of embodiments 3-8, wherein stimulation to a cervical level is to a region over C4-C5, over C3-C5, over C4-C6, over C3-C6, over C2-C5, over C3-C7, or over C3 to C7.

Embodiment 11

The method according to any one of embodiments 3-10, wherein stimulation to a thoracic level is to a region over at least one of T1 to T12, at least two of T1 to T12, at least three of T1 to T12, at least four of T1 to T12, at least five of T1 to T12, at least six of T1 to T12, at least seven of T1 to T12, at least 8 of T1 to T12, at least 9 of T1 to T12, at least 10 of T1 to T12, at least 11 of T1 to T12, or T1 to T12.

Embodiment 12

The method of embodiment 11, wherein stimulation to a thoracic level is to a region over T1 to T6, over a region of T11-T12, T10-T12, T9-T12, T8-T12, T8-T11, T8 to T10, T8 to T9, T9-T12, T9-T11, T9-T10, or T11-T12.

Embodiment 13

The method according to any one of embodiments 3-10, wherein stimulation to a lumbar level is to a region over at least one of L1-L5, over at least two of L1-L5, over at least three of L1-L5, over at least four of L1-L5, or L1-L5.

Embodiment 14

The method of embodiment 2-3, wherein said transcutaneous electrical spinal cord stimulation is applied paraspinally over C4-C5, T11-T12, or L1-L2 vertebrae.

Embodiment 15

The method according to any one of embodiments 2-3, and 8, wherein said transcutaneous electrical spinal cord stimulation is applied paraspinally over regions including one or more of C4-C5, T11-T12, or L1-L2 vertebrae.

Embodiment 16

The method of embodiment 15, wherein said transcutaneous electrical spinal cord stimulation is applied paraspinally over regions including two or more of C4-C5, T11-T12, or L1-L2 vertebrae.

Embodiment 17

The method according to any one of embodiments 2-3, and 8, wherein said transcutaneous electrical spinal cord stimulation is applied paraspinally over one or more of C4-C5, T11-T12, or L1-L2 vertebrae.

Embodiment 18

The method of embodiment 17, wherein said transcutaneous electrical spinal cord stimulation is applied paraspinally over two or more of C4-C5, T11-T12, or L1-L2 vertebrae.

Embodiment 19

The method of embodiment 17, wherein said transcutaneous electrical spinal cord stimulation is applied paraspinally over C4-C5, T11-T12, and L1-L2 vertebrae.

Embodiment 20

The method according to any one of embodiments 1-21, wherein said transcutaneous electrical stimulation is painless transcutaneous electrical stimulation (PTES).

Embodiment 21

The method according to any one of embodiments 1-20, wherein said transcutaneous stimulation is applied at an intensity ranging from about 30 to 200 mA, about 110 to 180 mA, about 10 mA to about 150 mA, from about 20 mA to about 100 mA, from about 30 or 40 mA to about 70 mA or 80 mA.

Embodiment 22

The method according to any one of embodiments 1-21, wherein said transcutaneous stimulation is applied at a frequency ranging from about 1 Hz to about 100 Hz, from about 3 Hz to about 90 Hz, from about 5 Hz to about 80 Hz, from about 5 Hz to about 30 Hz, or about 40 Hz, or about 50 Hz.

Embodiment 23

The method according to any one of embodiments 1-22, wherein said mammal has a spinal cord injury.

Embodiment 24

The method of embodiment 23, wherein said spinal cord injury is clinically classified as motor complete.

Embodiment 25

The method of embodiment 23, wherein said spinal cord injury is clinically classified as motor incomplete.

Embodiment 26

The method according to any one of embodiments 1-22, wherein said mammal has an ischemic brain injury.

Embodiment 27

The method of embodiment 26, wherein said ischemic brain injury is brain injury from stroke or acute trauma.

Embodiment 28

The method according to any one of embodiments 1-22, wherein said mammal has a neurodegenerative brain injury.

Embodiment 29

The method of embodiment 28, wherein said neurodegenerative brain injury is brain injury associated with a condition selected from the group consisting of Parkinson's disease, Huntington's disease, Alzhiemers, ischemic, stroke, amyotrophic lateral sclerosis (ALS), primary lateral sclerosis (PLS), dystonia, and cerebral palsy.

Embodiment 30

The method according to any one of embodiments 1-29, wherein said locomotor/motor activity includes standing, stepping, reaching, grasping, speech, swallowing, or breathing.

Embodiment 31

The method according to any one of embodiments 1-30, wherein said locomotor activity includes a walking motor pattern.

Embodiment 32

The method according to any one of embodiments 1-31, wherein said locomotor activity includes sitting down, laying down, sitting up, or standing up.

Embodiment 33

The method according to any one of embodiments 1-32, wherein the stimulation is under control of the subject.

Embodiment 34

The method according to any one of embodiments 1-33, wherein said method further includes physical training of said mammal

Embodiment 35

The method of embodiment 34, wherein said physical training includes inducing a load bearing positional change in said mammal

Embodiment 36

The method according to embodiment 34, wherein the load bearing positional change in said subject includes standing.

Embodiment 37

The method according to embodiment 34, wherein the load bearing positional change in said subject includes stepping.

Embodiment 38

The method according to any one of embodiments 34-37, wherein said physical training includes robotically guided training.

Embodiment 39

The method according to any one of embodiments 1-38, wherein said method further includes administration of one or more neuropharmaceuticals.

Embodiment 40

The method of embodiment 39, wherein said neuropharmaceutical includes one or more agents selected from the group consisting of a serotonergic drug, a dopaminergic drug, and a noradrenergic drug.

Embodiment 41

The method of embodiment 39, wherein said neuropharmaceutical includes a serotonergic drug.

Embodiment 42

The method of embodiment 41, wherein said neuropharmaceutical includes the serotonergic drug 8-OHDPAT.

Embodiment 43

The method according to any one of embodiments 39-42, wherein said neuropharmaceutical includes the serotonergic drug Way 100.635.

Embodiment 44

The method according to any one of embodiments 39-43, wherein said neuropharmaceutical includes the serotonergic drug Quipazine

Embodiment 45

The method according to any one of embodiments 39-44, wherein said neuropharmaceutical includes the serotonergic drug Ketanserin, SR 57227A.

Embodiment 46

The method according to any one of embodiments 39-45, wherein said neuropharmaceutical includes the serotonergic drug Ondanesetron

Embodiment 47

The method according to any one of embodiments 39-46, wherein said neuropharmaceutical includes the serotonergic drug SB269970.

Embodiment 48

The method according to any one of embodiments 39-47, wherein said neuropharmaceutical includes a dopaminergic drug.

Embodiment 49

The method according to any one of embodiments 39-48, wherein said neuropharmaceutical includes the dopaminergic drug SKF-81297.

Embodiment 50

The method according to any one of embodiments 39-49, wherein said neuropharmaceutical includes the dopaminergic drug SCH-23390.

Embodiment 51

The method according to any one of embodiments 39-50, wherein said neuropharmaceutical includes the dopaminergic drug Quinipirole.

Embodiment 52

The method according to any one of embodiments 39-51, wherein said neuropharmaceutical includes the dopaminergic drug Eticlopride.

Embodiment 53

The method according to any one of embodiments 39-52, wherein said neuropharmaceutical includes a noradrenergic drug.

Embodiment 54

The method according to any one of embodiments 39-53, wherein said neuropharmaceutical includes the noradrenergic drug Methoxamine.

Embodiment 55

The method according to any one of embodiments 39-54, wherein said neuropharmaceutical includes the noradrenergic drug Prazosin.

Embodiment 56

The method according to any one of embodiments 39-55, wherein said neuropharmaceutical includes the noradrenergic drug Clonidine.

Embodiment 57

The method according to any one of embodiments 39-56, wherein said neuropharmaceutical includes the noradrenergic drug Yohimbine.

Embodiment 58

An electrical stimulator said stimulator configured to induce locomotor or motor activity in a mammal according to anyone of embodiments 1-54.

Embodiment 59

An electrical stimulator according to embodiment 58 in combination with the pharmaceutical as recited in any one of embodiments 39-57 for use in inducing or restoring locomotor function in a mammal

Embodiment 60

The electrical stimulator of embodiment 59, wherein said mammal has a spinal cord injury.

Embodiment 61

The electrical stimulator of embodiment 60, wherein said spinal cord injury is clinically classified as motor complete.

Embodiment 62

The electrical stimulator of embodiment 60, wherein said spinal cord injury is clinically classified as motor incomplete.

Embodiment 63

The electrical stimulator of embodiment 60, wherein said mammal has an ischemic brain injury.

Embodiment 64

The electrical stimulator of embodiment 63, wherein said ischemic brain injury is brain injury from stroke or acute trauma.

Embodiment 65

The electrical stimulator of embodiment 60, wherein said mammal has a neurodegenerative brain injury.

Embodiment 66

The electrical stimulator of embodiment 65, wherein said neurodegenerative brain injury is brain injury associated with a condition selected from the group consisting of Parkinson's disease, Huntington's disease, Alzhiemers, ischemic, stroke, amyotrophic lateral sclerosis (ALS), primary lateral sclerosis (PLS), dystonia, and cerebral palsy.

Illustrative, but non-limiting embodiments of the contemplated are described herein. Variations on these embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context

EXAMPLES

The following examples are offered to illustrate, but not to limit the claimed invention.

Example 1

Six non-injured individuals were tested while lying on their right side with their legs supported in a gravity-independent position. tSCS was delivered using a 2.5 cm round electrode placed midline on the skin between the spinous processes of C4-C5, T11-T12, and/or L1-L2 as a cathode and two 5.0×10.2 $cm^2$ rectangular plates made of conductive plastic placed symmetrically on the skin over the iliac crests as anodes. Bipolar rectangular stimuli (1-msec duration) with a carrier frequency of 10 kHz and at intensities ranging from 30 to 200 mA were used. The stimulation was at 5 Hz and the exposure ranged from 10 to 30 sec. The threshold intensity of tSCS applied at T12 that induced involuntary stepping movements ranged from 110 to 180 mA. The same intensity was used during stimulation of C5 and/or L2. The strongest facilitation of stepping movements occurred when tSCS was applied at all three levels simultaneously. The multi-segmental stimulation of the cervical, thoracic, and lumbar spinal cord initiated stepping movements that had a short latency of initiation (~1 sec) and reached maximal amplitude within seconds. These data suggest that the synergistic and interactive effects of multi-site stimulation reflect the multi-segmental convergence of descending and ascending, and most likely propriospinal, influences on the spinal neuronal circuitry associated with locomotor activity. These data demonstrate the potential of a non-invasive means of stimulating the spinal cord, providing a new tool for modulating spinal locomotor circuitries and facilitating locomotion after a spinal cord injury.

Example

Experimental Methods

Animal Study:

Twelve adult female Sprague-Dawley rats (200-250 g body weight) underwent EMG and epidural stimulating electrode implantations and spinal cord transection surgeries. All experimental procedures were approved by the University of California Los Angeles Chancellor's Animal Research Committee and complied with the guidelines of the National Institutes of Health Guide for the Care and Use of Laboratory Animals.

Bipolar intramuscular EMG electrodes were implanted in the vastus lateralis (VL), semitendinosus (St), medial gastrocnemius (MG), and tibialis anterior (TA) muscles. Epidural electrodes were implanted at the L2 and S1 spinal segments. Spinal cord transection at T7-T8 was performed 14 days after the implantation of the EMG electrodes. Post-surgery, the bladders of all animals were expressed manually three times daily for the first two weeks and two times thereafter throughout the study. All of these procedures are performed routinely in our lab (Gerasimenko et al. (2007) *J. Neurophysiol.* 98: 2525-2536). The rats were trained 5 days/week, 20 min/session for 3 weeks (15 training sessions) starting 7 days after the spinal cord transection surgery. The treadmill belt speed was increased progressively from 6 to 13.5 cm/s.

All rats were tested in the presence of epidural stimulation at spinal segments L2 or S1 (monopolar stimulation) or at L2 and S1 simultaneously at intensities of 2.5 to 3.5 V. A stimulation frequency of 40 Hz with 200 μs duration rectangular pulses was used during monopolar stimulation. For simultaneous stimulation, the stimulation frequency at L2 was set to 40 Hz whereas the stimulation frequency at S1 varied (5, 10, 20, or 40 Hz).

Human Study.

Figure 2:
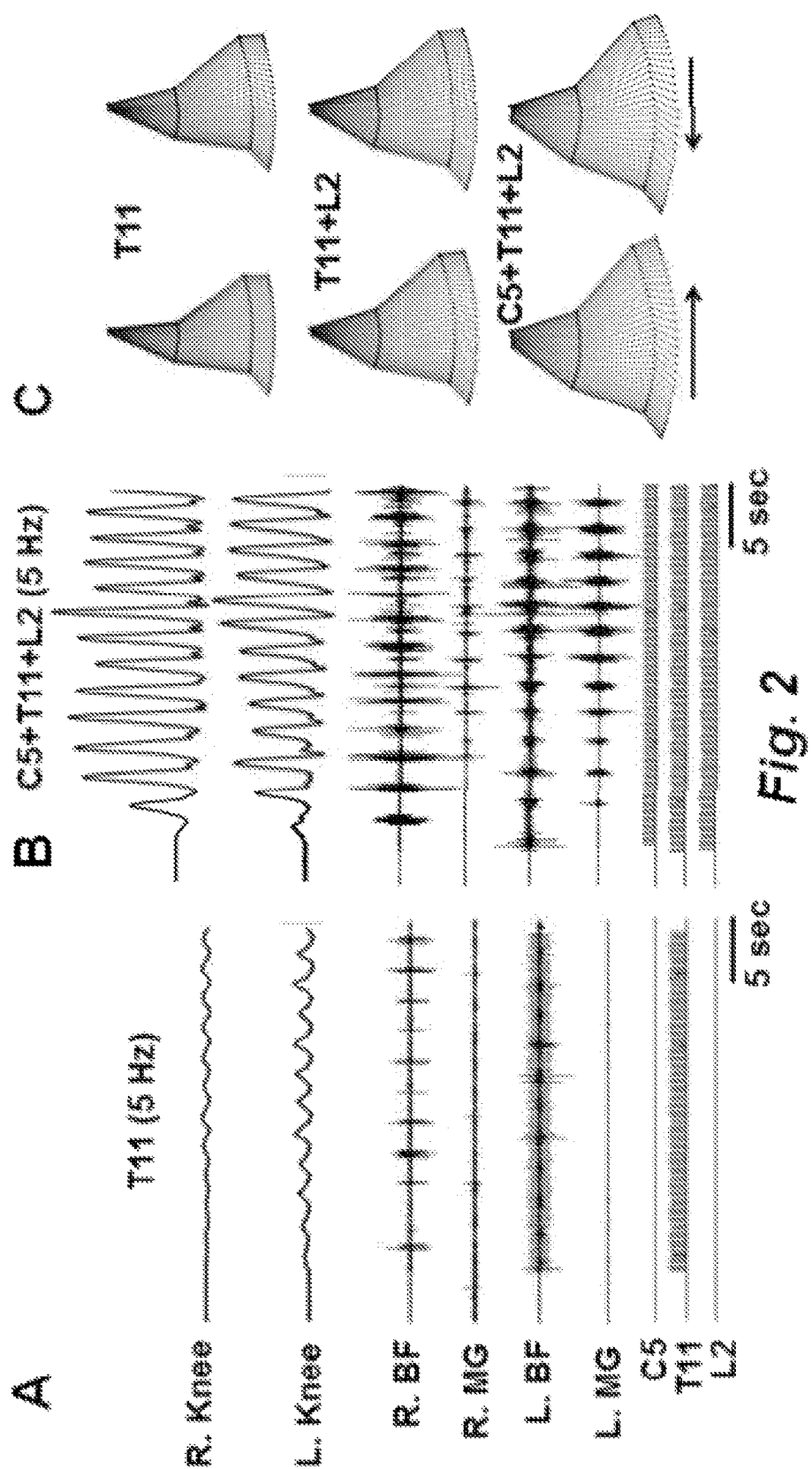
FIG. 2, panels A-C, provide an illustrative, but non-limiting, example of EMG and kinematic features of locomotor patterns induced by painless transcutaneous electrical spinal cord stimulation at the C5, T11, and L2 vertebral levels in non-injured human subjects. Panels A, B: Angular movements of the right (R) knee and left (L) knee joints and representative EMG activity in the biceps femoris (BF) and medial gastrocnemius (MG) muscles of the right (R) and left (L) legs during involuntary locomotor-like activity induced by transcutaneous spinal cord stimulation applied at the T11 vertebra alone (panel A) and at the C5+T11+L2 vertebrae simultaneously (panel B). Panel C: Stick diagram decompositions (40 ms between sticks) of the movements of the right leg during one step cycle during transcutaneous spinal cord stimulation at T11, T11+L2, and C5+T11+L2 simultaneously. Arrows indicate the direction of movement.

Six non-injured individuals participated in this study. The subjects were tested while lying on their right side with the upper leg supported directly in the area of the shank and the lower leg placed on a rotating brace attached to a horizontal board supported by vertical ropes secured to hooks in the ceiling as described previously (Gerasimenko et al. (2010) *J. Neurosci.* 30: 3700-3708). The subjects were instructed not to voluntarily intervene with the movements induced by the stimulation. Painless transcutaneous electrical stimulation (PTES) was delivered using a 2.5 cm round electrode (Lead_Lok, Sandpoint, United States) placed midline on the skin between the spinous processes of C4-C5, T11-T12 and L1-L2 as a cathode and two 5.0×10.2 cm2 rectangular plates made of conductive plastic (Ambu, Ballerup, Germany) placed symmetrically on the skin over the iliac crests as anodes. Step-like movements were evoked by bipolar rectangular stimuli with 0.5 ms duration filled with a carrier frequency of 10 kHz and at an intensity ranging from 30 to 200 mA. The stimulation frequency was 5 Hz and the duration of exposure ranged from 10 to 30 s. Bilateral EMG activity was recorded from the biceps femoris, and medial gastrocnemius muscles throughout the entire testing period using bipolar surface electrodes. EMG signals were amplified by a ME 6000 16-channel telemetric electroneuromyograph (MegaWin, Finland). Flexion—extension movements at the knee joints were recorded. (training sessions) starting 7 days after the using goniometers. Reflective markers were placed bilaterally on the lateral epicondyle of the humerus, greater trochanter, lateral epicondyle of the femur, lateral malleolus, and hallux. Kinematics measures of leg movements were recorded using the Qualisy video system (Sweden). A single step cycle during stable stepping is illustrated to show the coordination between joint movements (FIG. 2, panel C).

Example 3

Effects of Combinations of Epidural Stimulation on Hindlimb EMG Activity in Spinal Rats Among all combinations of epidural stimulation parameters used to evoke bipedal stepping in spinal rats, simultaneous stimulation at L2 (40 Hz) and S1 (5-15 Hz) produced the most coordinated and robust EMG stepping pattern in the hindlimb muscles. FIG. 1 shows the mean (14 steps/condition) peak EMG amplitudes of the antigravity muscle, in response to different combinations of epidural stimulation in a spinal rat. The peak amplitudes of filtered raw EMG signals from the same rat were 25-fold higher in all hindlimb muscles when tested during simultaneous epidural stimulation at L2 (40 Hz) and S1 (20 Hz) compared to L2 monopolar stimulation.

Example 4

PTES-Induced Involuntary Locomotor-Like Activity in Human Subjects

PTES was easily tolerated by subjects and did not cause pain even when the strength of current was increased to 200 mA. Lack of pain can be attributed to the use of biphasic stimuli with a carrier frequency of 10 kHz that suppresses the sensitivity of pain receptors. The threshold intensity of the stimulus that induced involuntary stepping movements ranged from 110 to 180 mA. PTES at a frequency of 5 Hz applied to T11 alone caused step-like movements in five out of the six tested subjects (see FIG. 2, panel A). The involuntary stepping movements induced by PTES were reflected in the alternating EMG bursting activity in symmetric muscles of the left and right legs as well as the alternation of the EMG bursts in antagonist muscles of the hip and shank. These movements were further facilitated with simultaneous stimulation at either C5 or L2. The strongest facilitation of stepping movements occurred when PTES was applied at all three levels simultaneously (see FIG. 2, panel B).

The multi-segmental stimulation of the cervical, thoracic, and lumbar spinal cord initiated stepping movements had a short latency of initiation (~1 sec) and reached maximal amplitude within sec (see FIG. 2, panel B). Importantly, immediately after simultaneous PTES of the cervical, thoracic, and lumbar spinal cord, the right and left knees moved in opposite directions clearly reflecting a distinct alternating stepping pattern (see FIG. 2, panel C). Although the kinematics (joint angles, trajectory characteristics) of the lower limb movements were qualitatively similar during PTES at T11, T11+L2, or C5+T11+L2, stimulation at the three spinal levels simultaneously produced flexion-extension movements with larger amplitudes than stimulation at either one or two segments (see FIG. 2, panel C).

The obtained results from both spinal rats and human subjects suggest that simultaneous spinal cord stimulation at multiple sites has an interactive effect on the spinal neural circuitries responsible for generating locomotion. Thus, in some embodiments, simultaneous multisite epidural stimulation with specific parameters can allow for a more precise control of these postural-locomotor interactions, resulting in robust, coordinated plantar full weight-bearing stepping in complete spinal rats. For example, the EMG stepping pattern during simultaneous multi-site epidural stimulation was significantly improved compared to bipolar stimulation between L2 and S1 or monopolar stimulation at L2 or S1 (FIG. 1). An added benefit of second-site (S1 added to L2) stimulation with specific parameters may be related to activation of postural neuronal circuitries and activation of rostrally projecting propriospinal neurons from the more caudal segments that contribute to the rhythm and pattern of output of the locomotor circuitry.

In some embodiments, accessing the lumbosacral locomotor circuitry can be accomplished using the present methods in a noninvasive, pain-free procedure. In other embodiments of the present methods, PTES applied to the same level of the spinal cord is also able to activate locomotor circuitry. In still other embodiments, the present methods can use multi-segmental non-invasive electrical spinal cord stimulation to facilitate involuntary, coordinated stepping movements.

Further, the present methods can provide synergistic and interactive effects of stimulation in both animals and humans. This synergistic and interactive effect can result from a multi-segmental convergence of descending and ascending, for example, propriospinal, influences on the spinal neuronal circuitries associated with locomotor and postural activity.

Example 5

In other embodiments, stepping movements can be enhanced when the spinal cord is stimulated at two to three spinal levels (e.g., C5, T12, and/or L2) simultaneously.

Figure 3:
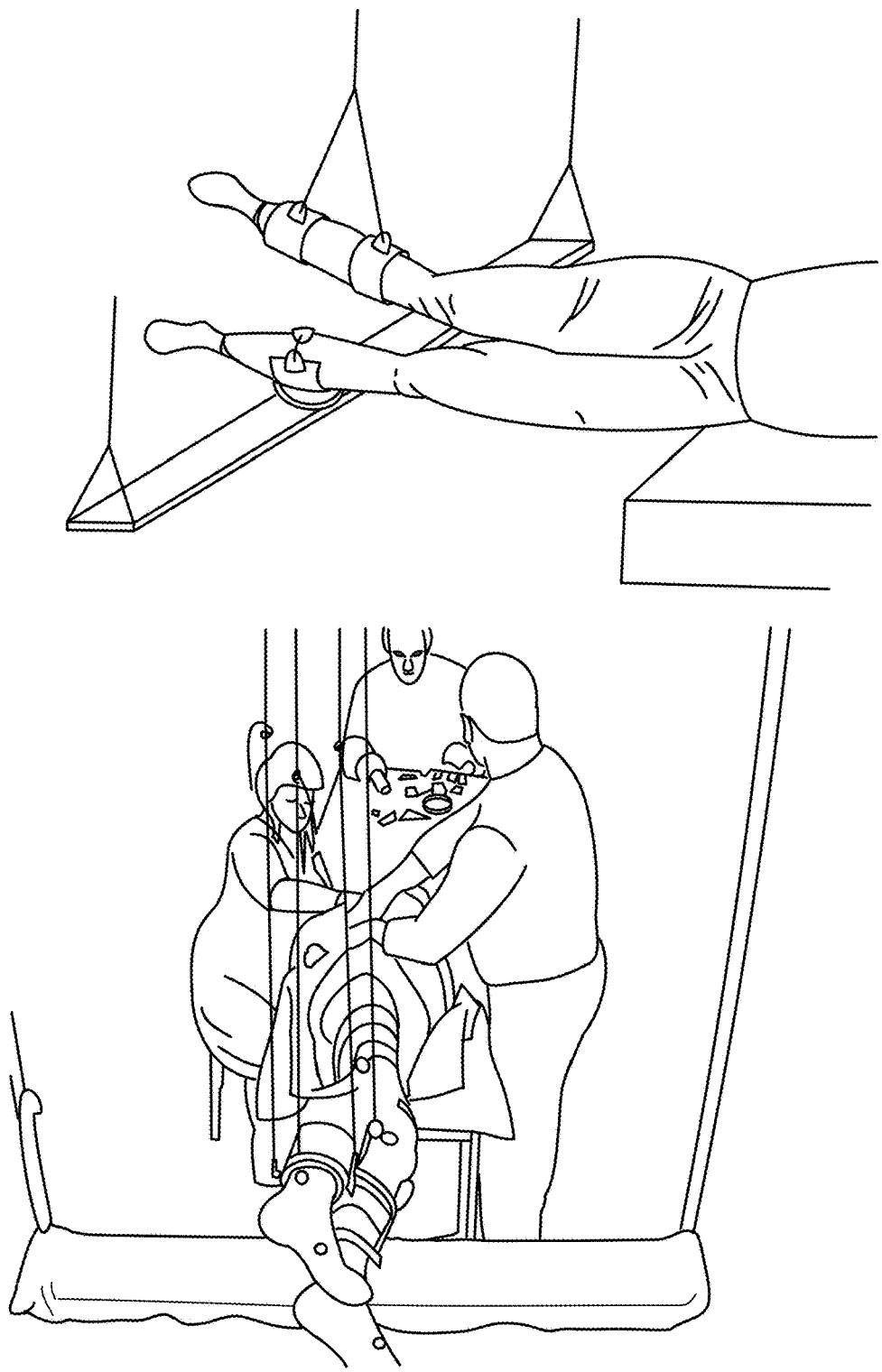
FIG. 3 is one example embodiment illustrating the positioning of test subjects

The subjects were tested while lying on their right side with the upper leg supported directly in the area of the shank and the lower leg placed on a rotating brace attached to a horizontal board supported by vertical ropes secured to hooks in the ceiling (FIG. 3). The subjects were instructed not to voluntarily intervene with the movements induced by the stimulation. Painless transcutaneous electrical stimulation (PTES) was delivered using a 2.5 cm round electrode (Lead_Lok, Sandpoint, United States) placed midline on the skin between the spinous processes of C4-C5, T11-T12 and L1-L2 as a cathode and two 5.0×10.2 cm$^2$ rectangular plates made of conductive plastic (Ambu, Ballerup, Germany) placed symmetrically on the skin over the iliac crests as anodes. Step-like movements were evoked by bipolar rectangular stimuli with 0.5 ms duration filled with a carrier frequency of 10 kHz and at an intensity ranging from 30 to 200 mA. The stimulation frequency was 5 Hz and the duration of exposure ranged from 10 to 30s.

Figure 4:
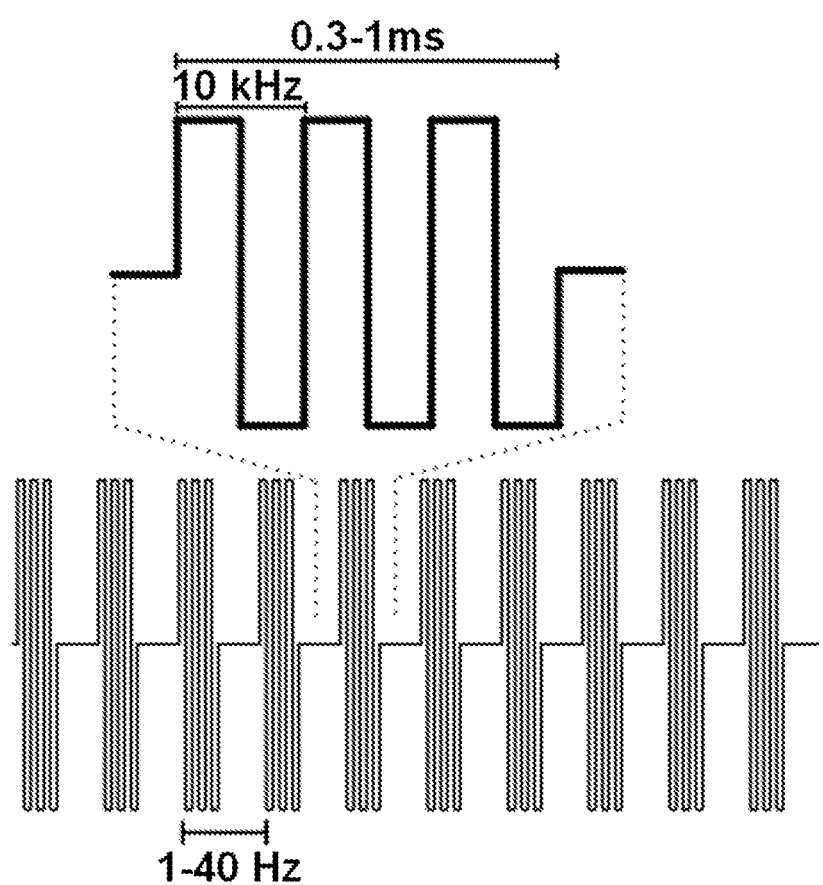
FIG. 4 is one example embodiment illustrating a graph depicting a 10 kHz biphasic stimulation is delivered in 0.3 to 1 ms. These pulses are delivered at 1-40 Hz.

TES was easily tolerated by subjects and did not cause pain even when the strength of current was increased to 200 mA. Lack of pain can be attributed to the use of biphasic stimuli with a carrier frequency of 10 kHz that suppresses the sensitivity of pain receptors. The threshold intensity of the stimulus that induced involuntary stepping movements ranged from 110 to 180 mA (FIG. 4).

Figure 5A:
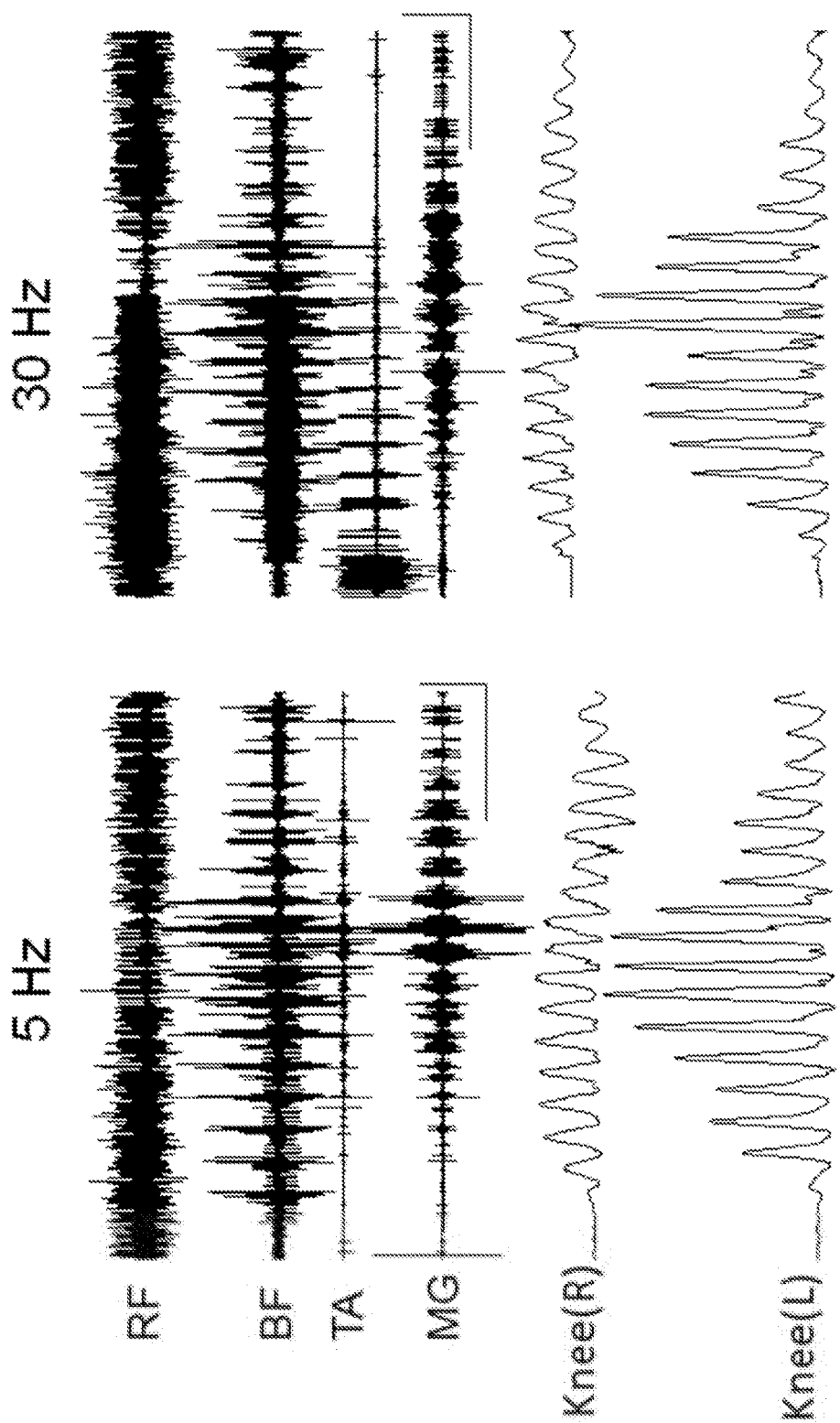
FIGS. 5A and 5B are examples of an embodiment illustrating EMG and kinematic features of locomotor patterns induced by painless transcutaneous electrical spinal cord stimulation at the T11-T12 vertebral level at 5 and 30 Hz of frequency in non-injured human subjects.
Figure 5B:
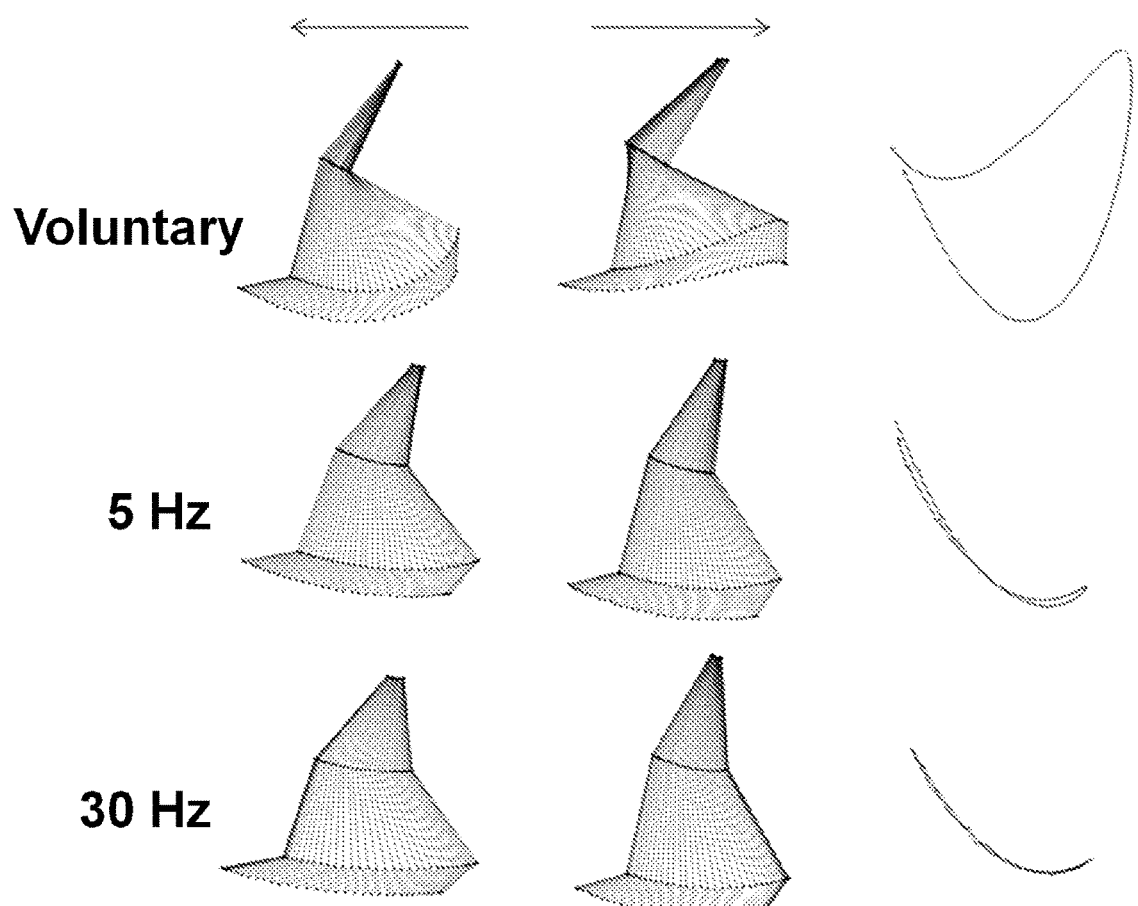

MG and kinematics features of locomotor patterns induced by painless transcutaneous electrical stimulation at the T11-T12 vertebral level at 5 and 30 Hz of frequency in non-injured human subjects are shown in FIGS. 5A and 5B. Angular movements of the right (R) knee and left (L) knee joints and representative EMG activity in the rectus femoris (RF), biceps femoris (BF) tibialis anterior (TA) and medial gastrocnemius (MG) muscles during involuntary locomotor-like activity induced by PTES at the T11 vertebra. Stick diagram decompositions (40 ms between sticks) of the movements of the R leg and trajectory of toe movements during one step cycle during PTES at T11-T12 are shown in FIG. 5B. Arrows in FIG. 5B indicate the direction of movement.

Figure 6:
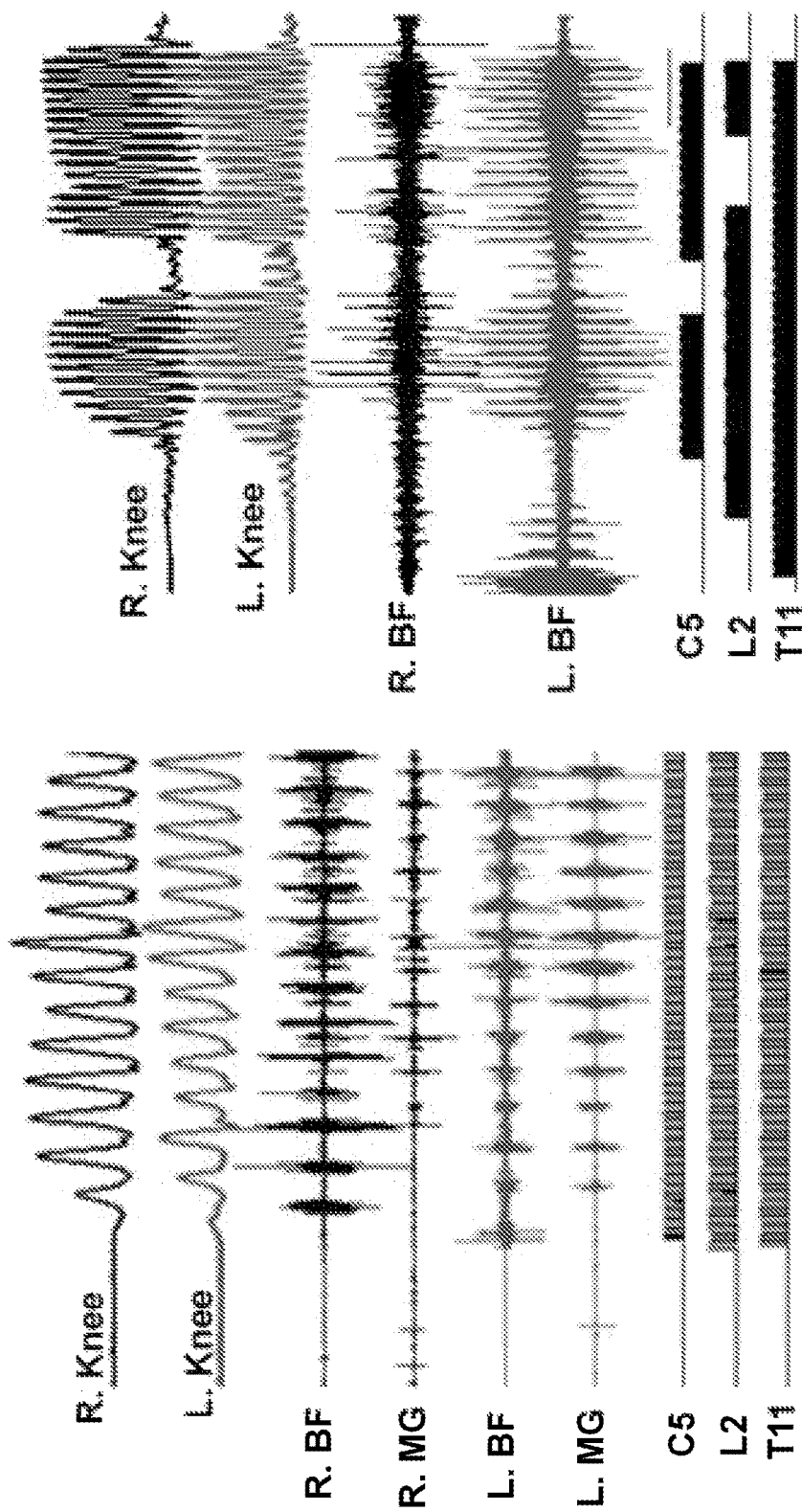
FIG. 6 is an example of one embodiment illustrating EMG and kinematic features of locomotor patterns induced by transcutaneous spinal cord stimulation at the C5, T11, and L2 vertebral levels. Angular movements of the right (R) knee and left (L) knee joints and representative EMG activity in the biceps femoris (BF) muscles of the R and left L legs during involuntary locomotor-like activity induced by transcutaneous spinal cord stimulation at the C5+T11+L2 vertebrae simultaneously (left) and sequentially (right).

EMG and kinematics features of locomotor patterns induced by PTES at the C5, T11, and L2 vertebral levels (FIG. 6). Angular movements of the right (R) knee and left (L) knee joints and representative EMG activity in the biceps femoris (BF) muscles of the R and left L legs during involuntary locomotor-like activity induced by PTES at the C5+T11+L2 vertebrae simultaneously (left) and sequentially (right).

Figure 7:
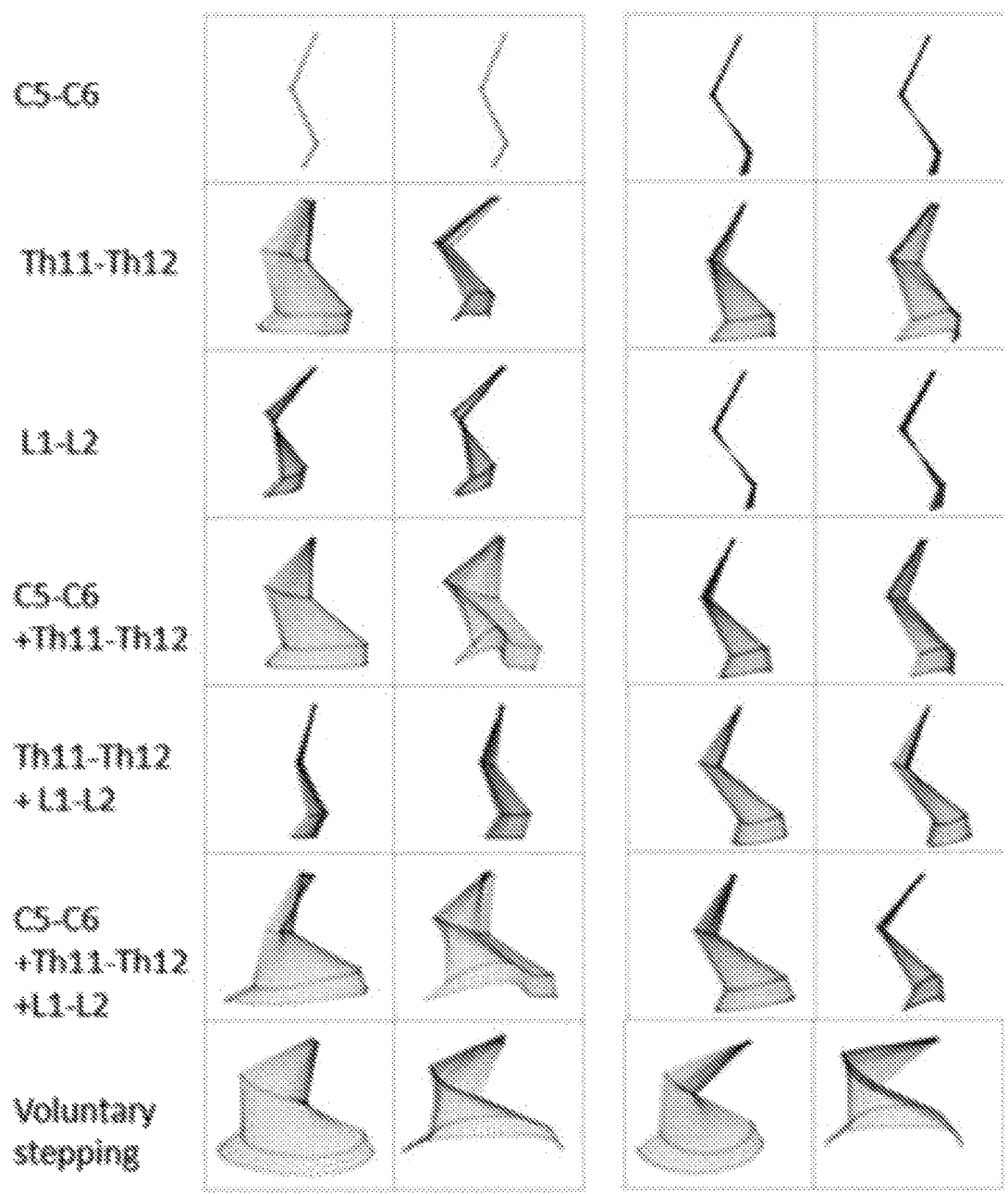
FIG. 7 is an example of one embodiment illustrating stick diagram decompositions (40 ms between sticks) of the movements of the R leg during one step cycle during transcutaneous spinal cord stimulation at different vertebral levels in two subjects are shown. Arrows indicate the direction of movement.

FIG. 7 shows stick diagram decompositions (40 ms between sticks) of the movements of the R leg during one step cycle during PTES at different vertebral levels in two subjects are shown. Arrows indicate the direction of movement. Multi-segmental non-invasive electrical spinal cord stimulation was used to facilitate involuntary, coordinated stepping movements. Simultaneous spinal cord stimulation at multiple sites can have an interactive effect on the spinal neural circuitries responsible for generating locomotion. The synergistic and interactive effects of multi-site spinal cord stimulation can be a multi-segmental convergence of descending and ascending, and most likely propriospinal, influences on the spinal circuitries associated with locomotor and postural activity.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of facilitating locomotor activity in a mammal having a spinal cord or brain injury, said method comprising administering transcutaneous electrical stimulation to the spinal cord of said mammal at a frequency and intensity that facilitates the recovery or improved control of said locomotor activity, wherein said stimulation is applied at two or more locations over the spinal cord, stimulates spinal circuitry, and enables or induces a locomotor pattern in said mammal.

2. The method of claim 1, wherein said mammal is a human.

3. The method of claim 2, wherein said transcutaneous electrical spinal cord stimulation is applied paraspinally over C4-C5, T11-T12 and/or L1-L2 vertebrae.

4. The method of claim 1, wherein said transcutaneous stimulation is applied at an intensity ranging from about 30 to 200 mA.

5. The method of claim 1, wherein said transcutaneous stimulation is applied at a frequency ranging from about 3 Hz to about 100 Hz.

6. The method of claim 1, wherein said mammal has a spinal cord injury and/or an ischemic brain injury, and/or a neurodegenerative brain injury.

7. The method of claim 6, wherein said mammal has a spinal cord injury clinically classified as motor complete.

8. The method of claim 6, wherein said mammal has a spinal cord injury clinically classified as motor incomplete.

9. The method of claim 6, wherein said mammal has an ischemic brain injury brain injury from stroke or acute trauma.

10. The method of claim 6, wherein said mammal has a neurodegenerative brain injury associated with a condition selected from the group consisting of Parkinson's disease, Huntington's disease, Alzheimer's, ischemic stroke, amyotrophic lateral sclerosis (ALS), primary lateral sclerosis (PLS), and cerebral palsy.

11. The method of claim 1, wherein said locomotor activity comprises one or more activities selected from the group consisting of standing, stepping, speech, swallowing or breathing, a walking motor pattern, sitting down, and laying down.

12. The method of claim 1, wherein said mammal is a human and the stimulation is under control of said human.

13. The method of claim 1, wherein said method further comprises physical training of said mammal.

14. The method of claim 13, wherein said physical training comprises inducing a load bearing positional change in said mammal, and/or standing, and/or stepping.

15. The method of claim 13, wherein said physical training comprises robotically guided training.

16. The method of claim 1, wherein said method further comprises administration of one or more neuropharmaceuticals.

17. The method of claim 16, wherein said neuropharmaceutical comprises one or more agents selected from the group consisting of a serotonergic drug, a dopaminergic drug, and a noradrenergic drug.

18. The method of claim 1, wherein said transcutaneous electrical spinal cord stimulation is administered to two or more spinal levels simultaneously.

19. The method of claim 18, wherein said two or more spinal levels comprise spinal levels selected from the group consisting of the brain stem, cervical, thoracic, thoraco-lumbar, lumbar, lumbo-sacral, and sacrum.

20. The method of claim 1, wherein said method enables voluntary movement of muscles involved in at least one of standing, stepping, reaching, grasping, voluntarily changing positions of one or both legs.

21. The method of claim 1, wherein said transcutaneous stimulation is applied at a frequency ranging from about 5 Hz to about 40 Hz.

22. The method of claim 1, wherein said transcutaneous stimulation is applied at an intensity ranging from about 20 mA to about 100 mA.

23. The method of claim 1, wherein said transcutaneous stimulation is provided on a high frequency carrier of about 10 kHz.

* * * * *